(12) United States Patent
Davalos et al.

(10) Patent No.: US 8,282,631 B2
(45) Date of Patent: *Oct. 9, 2012

(54) TISSUE ABLATION WITH IRREVERSIBLE ELECTROPORATION

(75) Inventors: Rafael Davalos, Oakland, CA (US); Boris Rubinsky, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/237,199

(22) Filed: Sep. 20, 2011

(65) Prior Publication Data

US 2012/0071874 A1    Mar. 22, 2012

Related U.S. Application Data

(63) Continuation of application No. 10/571,162, filed as application No. PCT/US2004/043477 on Dec. 21, 2004, now Pat. No. 8,048,067.

(60) Provisional application No. 60/532,588, filed on Dec. 24, 2003.

(51) Int. Cl.
*A61B 18/18* (2006.01)

(52) U.S. Cl. ........................................................ 606/32

(58) Field of Classification Search ............... 606/32–50
See application file for complete search history.

(56) References Cited

U.S. PATENT DOCUMENTS

| | | |
|---|---|---|
| 1,653,819 A | 12/1927 | Northcott et al. |
| 4,016,886 A | 4/1977 | Doss |
| 4,226,246 A | 10/1980 | Fragnet |
| 4,262,672 A | 4/1981 | Kief |
| 4,407,943 A | 10/1983 | Cole et al. |
| 4,810,963 A | 3/1989 | Blake-Coleman et al. |
| 4,907,601 A | 3/1990 | Frick |
| 4,946,793 A | 8/1990 | Marshall, III |
| 5,019,034 A | 5/1991 | Weaver et al. |
| 5,052,391 A | 10/1991 | Silberstone et al. |
| 5,058,605 A | 10/1991 | Slovak |
| 5,098,843 A | 3/1992 | Calvin |

(Continued)

FOREIGN PATENT DOCUMENTS

DE    863111    1/1953

(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49-53.

(Continued)

*Primary Examiner* — Michael Peffley
*Assistant Examiner* — Ronald Hupczey, Jr.
(74) *Attorney, Agent, or Firm* — Karl Bozicevic; Bozicevic, Field & Francis LLP

(57) ABSTRACT

A new method for the ablation of undesirable tissue such as cells of a cancerous or non-cancerous tumor is disclosed. It involves the placement of electrodes into or near the vicinity of the undesirable tissue through the application of electrical pulses causing irreversible electroporation of the cells throughout the entire area of the undesirable tissue. The electric pulses irreversibly permeate the cell membranes, thereby invoking cell death. The irreversibly permeabilized cells are left in situ and are removed by the body immune system. The amount of tissue ablation achievable through the use of irreversible electroporation without inducing thermal damage is considerable.

40 Claims, 13 Drawing Sheets

U.S. PATENT DOCUMENTS

| | | | |
|---|---|---|---|
| 5,134,070 A | 7/1992 | Casnig | |
| 5,173,158 A | 12/1992 | Schmukler | |
| 5,193,537 A | 3/1993 | Freeman | |
| 5,273,525 A | 12/1993 | Hofmann | |
| 5,283,194 A | 2/1994 | Schmukler | |
| 5,318,563 A | 6/1994 | Malis et al. | |
| 5,328,451 A | 7/1994 | Davis et al. | |
| 5,389,069 A | 2/1995 | Weaver | |
| 5,403,311 A | 4/1995 | Abele et al. | |
| 5,425,752 A | 6/1995 | Vu'Nguyen | |
| 5,439,440 A | 8/1995 | Hofmann | |
| 5,458,625 A | 10/1995 | Kendall | |
| 5,533,999 A | 7/1996 | Hood et al. | |
| 5,536,240 A | 7/1996 | Edwards et al. | |
| 5,575,811 A | 11/1996 | Reid et al. | |
| 5,626,146 A | 5/1997 | Barber et al. | |
| 5,634,899 A | 6/1997 | Shapland et al. | |
| 5,674,267 A | 10/1997 | Mir et al. | |
| 5,702,359 A | 12/1997 | Hofmann | |
| 5,718,246 A | 2/1998 | Vona | |
| 5,720,921 A | 2/1998 | Meserol | |
| 5,778,894 A | 7/1998 | Dorogi et al. | |
| 5,782,882 A | 7/1998 | Lerman et al. | |
| 5,800,378 A | 9/1998 | Edwards et al. | |
| 5,807,306 A | 9/1998 | Shapland et al. | |
| 5,810,762 A | 9/1998 | Hofmann | |
| 5,836,905 A | 11/1998 | Lemelson et al. | |
| 5,843,026 A | 12/1998 | Edwards et al. | |
| 5,873,849 A | 2/1999 | Bernard | |
| 5,919,142 A | 7/1999 | Boone et al. | |
| 5,947,889 A | 9/1999 | Hehrlein | |
| 5,983,131 A | 11/1999 | Weaver et al. | |
| 5,991,697 A | 11/1999 | Nelson et al. | |
| 5,999,847 A | 12/1999 | Elstrom | |
| 6,009,347 A | 12/1999 | Hofmann | |
| 6,010,613 A * | 1/2000 | Walters et al. | 205/701 |
| 6,016,452 A | 1/2000 | Kasevich | |
| 6,041,252 A | 3/2000 | Walker et al. | |
| 6,055,453 A | 4/2000 | Hofmann et al. | |
| 6,068,650 A | 5/2000 | Hofmann et al. | |
| 6,085,115 A | 7/2000 | Weaver et al. | |
| 6,090,016 A | 7/2000 | Kuo | |
| 6,102,885 A | 8/2000 | Bass | |
| 6,106,521 A | 8/2000 | Blewett et al. | |
| 6,109,270 A | 8/2000 | Mah et al. | |
| 6,122,599 A | 9/2000 | Mehta | |
| 6,132,419 A | 10/2000 | Hofmann | |
| 6,159,163 A | 12/2000 | Strauss et al. | |
| 6,208,893 B1 * | 3/2001 | Hofmann | 604/21 |
| 6,210,402 B1 | 4/2001 | Olsen et al. | |
| 6,212,433 B1 | 4/2001 | Behl | |
| 6,216,034 B1 | 4/2001 | Hofmann | |
| 6,219,577 B1 | 4/2001 | Brown et al. | |
| 6,241,702 B1 | 6/2001 | Lundquist et al. | |
| 6,261,831 B1 | 7/2001 | Agee | |
| 6,278,895 B1 * | 8/2001 | Bernard | 604/20 |
| 6,300,108 B1 | 10/2001 | Rubinsky | |
| 6,326,177 B1 | 12/2001 | Schoenbach et al. | |
| 6,347,247 B1 | 2/2002 | Dev et al. | |
| 6,349,233 B1 | 2/2002 | Adams | |
| 6,351,674 B2 | 2/2002 | Silverstone | |
| 6,387,671 B1 * | 5/2002 | Rubinsky et al. | 435/173.7 |
| 6,403,348 B1 | 6/2002 | Rubinsky et al. | |
| 6,470,211 B1 | 10/2002 | Ideker et al. | |
| 6,482,619 B1 | 11/2002 | Rubinsky et al. | |
| 6,493,592 B1 | 12/2002 | Leonard et al. | |
| 6,500,173 B2 | 12/2002 | Underwood et al. | |
| 6,526,320 B2 | 2/2003 | Mitchell | |
| 6,562,604 B2 | 5/2003 | Rubinsky et al. | |
| 6,607,529 B1 | 8/2003 | Jones et al. | |
| 6,611,706 B2 | 8/2003 | Avrahami et al. | |
| 6,613,211 B1 | 9/2003 | McCormick et al. | |
| 6,627,421 B1 | 9/2003 | Unger et al. | |
| 6,653,091 B1 | 11/2003 | Dunn et al. | |
| 6,669,691 B1 | 12/2003 | Taimisto | |
| 6,692,493 B2 | 2/2004 | McGovern et al. | |
| 6,697,669 B2 | 2/2004 | Dev et al. | |
| 6,697,670 B2 | 2/2004 | Chornenky et al. | |
| 6,702,808 B1 | 3/2004 | Kreindel | |
| 6,795,728 B2 | 9/2004 | Chornenky et al. | |
| 6,801,804 B2 | 10/2004 | Miller et al. | |
| 6,865,416 B2 | 3/2005 | Dev et al. | |
| 6,892,099 B2 | 5/2005 | Jaafar et al. | |
| 6,912,417 B1 | 6/2005 | Bernard et al. | |
| 6,927,049 B2 | 8/2005 | Rubinsky et al. | |
| 6,962,587 B2 | 11/2005 | Johnson et al. | |
| 6,972,014 B2 | 12/2005 | Eum et al. | |
| 6,994,706 B2 * | 2/2006 | Chornenky et al. | 606/41 |
| 7,053,063 B2 | 5/2006 | Rubinsky et al. | |
| 7,063,698 B2 | 6/2006 | Whayne et al. | |
| 7,130,697 B2 | 10/2006 | Chornenky et al. | |
| 7,211,083 B2 | 5/2007 | Chornenky et al. | |
| 7,267,676 B2 | 9/2007 | Chornenky et al. | |
| 2001/0044596 A1 | 11/2001 | Jaafar | |
| 2002/0010491 A1 | 1/2002 | Schoenbach | |
| 2002/0055731 A1 | 5/2002 | Atala et al. | |
| 2002/0077314 A1 | 6/2002 | Falk et al. | |
| 2002/0077676 A1 | 6/2002 | Schroeppel et al. | |
| 2002/0099323 A1 | 7/2002 | Dev et al. | |
| 2002/0133324 A1 | 9/2002 | Weaver et al. | |
| 2002/0138117 A1 | 9/2002 | Son | |
| 2002/0193831 A1 | 12/2002 | Smith, III | |
| 2003/0009110 A1 | 1/2003 | Tu et al. | |
| 2003/0060856 A1 | 3/2003 | Chornenky et al. | |
| 2003/0088199 A1 | 5/2003 | Kawaji | |
| 2003/0130711 A1 * | 7/2003 | Pearson et al. | 607/101 |
| 2003/0170898 A1 | 9/2003 | Gundersen et al. | |
| 2003/0199050 A1 | 10/2003 | Mangano et al. | |
| 2003/0208200 A1 | 11/2003 | Palanker et al. | |
| 2003/0225360 A1 | 12/2003 | Eppstein et al. | |
| 2004/0019371 A1 | 1/2004 | Jaafar et al. | |
| 2004/0059389 A1 | 3/2004 | Chornenky et al. | |
| 2004/0146877 A1 | 7/2004 | Diss et al. | |
| 2004/0153057 A1 | 8/2004 | Davison | |
| 2004/0243107 A1 | 12/2004 | Mackoviak | |
| 2004/0267189 A1 | 12/2004 | Mavor et al. | |
| 2005/0043726 A1 | 2/2005 | McHale et al. | |
| 2005/0049541 A1 | 3/2005 | Behar et al. | |
| 2005/0165393 A1 | 7/2005 | Eppstein | |
| 2005/0171523 A1 | 8/2005 | Rubinsky et al. | |
| 2005/0171574 A1 | 8/2005 | Rubinsky et al. | |
| 2005/0182462 A1 | 8/2005 | Chornenky et al. | |
| 2005/0261672 A1 | 11/2005 | Deem et al. | |
| 2005/0288730 A1 | 12/2005 | Deem et al. | |
| 2006/0015147 A1 | 1/2006 | Persson et al. | |
| 2006/0025760 A1 * | 2/2006 | Podhajsky | 606/38 |
| 2006/0079883 A1 | 4/2006 | Elmouelhi et al. | |
| 2006/0121610 A1 | 6/2006 | Rubinsky et al. | |
| 2006/0212078 A1 | 9/2006 | Demarais et al. | |
| 2006/0217703 A1 | 9/2006 | Chornenky et al. | |
| 2006/0264752 A1 | 11/2006 | Rubinsky et al. | |
| 2007/0043345 A1 | 2/2007 | Davalos et al. | |
| 2007/0118069 A1 | 5/2007 | Persson et al. | |
| 2008/0021371 A1 | 1/2008 | Rubinsky | |
| 2008/0052786 A1 | 2/2008 | Lin et al. | |

FOREIGN PATENT DOCUMENTS

| | | |
|---|---|---|
| DE | 4000893 | 7/1991 |
| EP | 0378132 | 7/1990 |
| EP | 0935482 | 5/2005 |
| WO | 9639531 | 12/1996 |
| WO | 0020554 | 4/2000 |
| WO | 01/10319 | 2/2001 |
| WO | 0107583 | 2/2001 |
| WO | 0107584 | 2/2001 |
| WO | 0107585 | 2/2001 |
| WO | 0181533 | 11/2001 |
| WO | 02/078527 | 10/2002 |
| WO | 02/089686 | 11/2002 |
| WO | 02/100459 | 12/2002 |
| WO | 03/047684 | 6/2003 |
| WO | 03/099382 | 12/2003 |
| WO | 2004037341 | 5/2004 |

OTHER PUBLICATIONS

Andreason, Electroporation as a Technique for the Transfer of Macromolecules into Mammalian Cell Lines, *J. Tiss. Cult. Meth.*, 15:56-62, 1993.

Baker, et al., Calcium-Dependent Exocytosis in Bovine Adrenal Medullary Cells with Leaky Plasma Membranes, *Nature*, vol. 276, pp. 620-622, 1978.

Barber, Electrical Impedance Tomography Applied Potential Tomography, Advances in Biomedical Engineering, Beneken and Thevenin, eds., IOS Press, 1993, pp. 165-173.

Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105-A115.

Bown, S.G., Phototherapy of tumors. *World J. Surgery*, 1983. 7: p. 700-9.

BPH Management Strategies: Improving Patient Satisfaction, *Urology Times*, May 2001, vol. 29, Supplement 1.

Brown, et al., Blood Flow Imaging Using Electrical Impedance Tomography, *Clin. Phys. Physiol. Meas.*, 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001, p. 1210.

Coates, C.W., et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, *IEEE Transactions on Biomedical Engineering*, vol. 41, No. 8, Aug. 1994, pp. 713,722.

Cowley, Good News for Boomers, *Newsweek*, Dec. 30, 1996/Jan. 6, 1997, p. 1.

Cox, et al., Surgical Treatment of Atrial Fibrillation: A Review, *Europace* (2004) 5, S20-S-29.

Crowley, Electrical Breakdown of Biomolecular Lipid Membranes as an Electromechanical Instability, *Biophysical Journal*, vol. 13, pp. 711-724, 1973.

Davalos, et al., Tissue Ablation with Irreversible Electroporation, *Annals of Biomedical Engineering*, vol. 33, No. 2, Feb. 2005, pp. 223-231.

Davalos, et al., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor T issue Electroporation for Molecular Medicine, *IEEE Transactions on Biomedical Engineering*, vol. 49, No. 4, Apr. 2002, pp. 400-403.

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002, pp. 1-237.

Dean, Nonviral Gene Transfer to Skeletal, Smooth, and Cardiac Muscle in Living Animals, *Am J. Physiol Cell Physiol* 289: 233-245, 2005.

Dev, et al., Sustained Local Delivery of Heparin to the Rabbit Arterial Wall with an Electroporation Catheter, *Catheterization and Cardiovascular Diagnosis*, Nov. 1998, vol. 45, No. 3, pp. 337-343.

Dev, et al., Medical Applications of Electroporation, *IEEE Transactions of Plasma Science*, vol. 28, No. 1, pp. 206-223, Feb. 2000.

Duraiswami, et al., Boundary Element Techniques for Efficient 2-D and 3-D Electrical Impedance Tomography, *Chemical Engineering Science*, vol. 52, No. 13, pp. 2185-2196, 1997.

Duraiswami, et al., Efficient 2D and 3D Electrical Impedance Tomography Using Dual Reciprocity Boundary Element Techniques, *Engineering Analysis with Boundary Elements* 22, (1998) 13-31.

Duraiswami, et al., Solution of Electrical Impedance Tomography Equations Using Boundary Element Methods, *Boundary Element Technology* XII, 1997, pp. 226-237.

Edd, J., et al., In-Vivo Results of a New Focal Tissue Ablation Technique: Irreversible Electroporaton, *IEEE Trans. Biomed. Eng.* 53 (2006) p. 1409-1415.

Erez, et al., Controlled Destruction and Temperature Distributions in Biological Tissues Subjected to Monoactive Electrocoagulation, *Transactions of the ASME: Journal of Mechanical Design*, vol. 102, Feb. 1980, pp. 42-49.

Foster, R.S., et al., High-intensity focused ultrasound in the treatment of prostatic disease. *Eur. Urol.*, 1993. 23: 44-7.

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.*, vol. 48, No. 3, pp. 249-264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233-240.

Gençer, et al., Electrical Impedance Tomography: Induced-Current Imaging Achieved with a Multiple Coil System, *IEEE Transactions on Biomedical Engineering*, vol. 43, No. 2, Feb. 1996, pp. 139-149.

Gilbert, et al., Novel Electrode Designs for Electrochemotherapy, *Biochimica et Biophysica Acta* 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffiths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995, pp. 948-954.

Gumerov, et al., The Dipole Approximation Method and Its Coupling with the Regular Boundary Element Method for Efficient Electrical Impedance Tomography, *Boundary Element Technology* XIII, 1999, 10 pp.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

Ho, et al., Electroporation of Cell Membranes: A Review, *Critical Reviews in Biotechnology*, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

Huang, et al., Micro-Electroporation: Improving the Efficiency and Understanding of Electrical Permeabilization of Cells, *Biomedical Microdevices*, vol. 2, pp. 145-150, 1999.

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998, pp. 1-16.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA*, vol. 95, pp. 10356-10360, Sep. 1998.

Lurquin, Gene Transfer by Electroporation, *Molecular Biotechnology*, vol. 7, 1997, pp. 5-35.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Mir et al., "Mechanisms of Electrochemotherapy" Advanced Drug Delivery Reviews, (1999) 35:107-118.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997, pp. 167-172.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001, p. 1213.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Precision Office TUNA System, "When Patient Satisfaction is Your Goal", 11 pages, 2001.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed. Eng.* vol. 2 2000. 157-187.

Schmukler, Impedance Spectroscopy of Biological Cells, downloaded from IEEE Xplore website, 2009, p. 74a.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

Vidamed, Inc., Transurethral Needle Ablation (TUNA): Highlights from Worldwide Clinical Studies, Vidamed's Office TUNA System, 4 pages, 2001.

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology*, vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001, p. 1204.

* cited by examiner

TISSUE ABLATION WITH IRREVERSIBLE ELECTROPORATION

CROSS-REFERENCE

This application is a continuation of U.S. patent application Ser. No. 10/571,162, now U.S. Pat. No. 8,048,067, filed Oct. 18, 2006, which application is a 371 National Phase of US2004/043477 filed Dec. 21, 2004, which application claims the benefit of U.S. Provisional Application No. 60/532,588, filed Dec. 24, 2003, all of which applications are incorporated herein by reference.

FIELD OF THE INVENTION

This invention resides in the fields of electroporation of tissue and to treatments whereby tissue is destroyed by irreversible electroporation.

BACKGROUND OF THE INVENTION

In many medical procedures, such as the treatment of benign or malignant tumors, it is important to be able to ablate the undesirable tissue in a controlled and focused way without affecting the surrounding desirable tissue. Over the years, a large number of minimally invasive methods have been developed to selectively destroy specific areas of undesirable tissues as an alternative to resection surgery. There are a variety of techniques with specific advantages and disadvantages, which are indicated and contraindicated for various applications. For example, cryosurgery is a low temperature minimally invasive technique in which tissue is frozen on contact with a cryogen cooled probe inserted in the undesirable tissue (Rubinsky, B., ed. *Cryosurgery*. Annu. Rev. Biomed. Eng. Vol. 2. 2000. 157-187.). The area affected by low temperature therapies, such as cryosurgery, can be easily controlled through imaging. However, the probes are large and difficult to use. Non-selective chemical ablation is a technique in which chemical agents such as ethanol are injected in the undesirable tissue to cause ablation (Shiina, S., et al., *Percutaneous ethanol injection therapy for hepatocellular carcinoma: results in* 146 *patients*. AJR, 1993. 160: p. 1023-8). Non-selective chemical therapy is easy to apply. However, the affected area cannot be controlled because of the local blood flow and transport of the chemical species. Elevated temperatures are also used to ablate tissue. Focused ultrasound is a high temperature non-invasive technique in which the tissue is heated to coagulation using high-intensity ultrasound beams focused on the undesirable tissue (Lynn, J. G., et al., *A new method for the generation of use of focused ultrasound in experimental biology*. J. Gen Physiol., 1942. 26: p. 179-93; Foster, R. S., et al., *High-intensity focused ultrasound in the treatment of prostatic disease*. Eur. Urol., 1993. 23: p. 44-7). Electrical currents are also commonly used to heat tissue. Radiofrequency ablation (RF) is a high temperature minimally invasive technique in which an active electrode is introduced in the undesirable tissue and a high frequency alternating current of up to 500 kHz is used to heat the tissue to coagulation (Organ, L. W., *Electrophysiological principles of radiofrequency lesion making*. Appl. Neurophysiol., 1976. 39: p. 69-76). In addition to RF heating traditional Joule heating methods with electrodes inserted in tissue and dc or ac currents are also common, (Erez, A., Shitzer, A. (*Controlled destruction and temperature distribution in biological tissue subjected to monoactive electrocoagulation*) J. Biomech. Eng. 1980:102(1):42-9). Interstitial laser coagulation is a high temperature thermal technique in which tumors are slowly heated to temperatures exceeding the threshold of protein denaturation using low power lasers delivered to the tumors by optical fibers (Bown, S. G., *Phototherapy of tumors*. World. J. Surgery, 1983. 7: p. 700-9). High temperature thermal therapies have the advantage of ease of application. The disadvantage is the extent of the treated area is difficult to control because blood circulation has a strong local effect on the temperature field that develops in the tissue. The armamentarium of surgery is enhanced by the availability of the large number of minimally invasive surgical techniques in existence, each with their own advantages and disadvantages and particular applications. This document discloses another minimally invasive surgical technique for tissue ablation, irreversible electroporation. We will describe the technique, evaluate its feasibility through mathematical modeling and demonstrate the feasibility with in vivo experimental studies.

Electroporation is defined as the phenomenon that makes cell membranes permeable by exposing them to certain electric pulses (Weaver, J. C. and Y. A. Chizmadzhev, *Theory of electroporation: a review*. Bioelectrochem. Bioenerg., 1996. 41: p. 135-60). Electroporation pulses are defined as those electrical pulses that through a specific combination of amplitude, shape, time length and number of repeats produce no other substantial effect on biological cells than the permeabilization of the cell membrane. The range of electrical parameters that produce electroporation is bounded by: a) parameters that have no substantial effect on the cell and the cell membrane, b) parameters that cause substantial thermal effects (Joule heating) and c) parameters that affect the interior of the cell, e.g. the nucleus, without affecting the cell membrane. Joule heating, the thermal effect that electrical currents produce when applied to biological materials is known for centuries. It was noted in the previous paragraph that electrical thermal effects which elevate temperatures to values that damage cells are commonly used to ablate undesirable tissues. The pulse parameters that produce thermal effects are longer and/or have higher amplitudes than the electroporation pulses whose only substantial effect is to permeabilize the cell membrane.

There are a variety of methods to electrically produce thermal effects that ablate tissue. These include RF, electrode heating, and induction heating. Electrical pulses that produce thermal effects are distinctly different from the pulses which produce electroporation. The distinction can be recognizing through their effect on cells and their utility. The effect of the thermal electrical pulses is primarily on the temperature of the biological material and their utility is in raising the temperature to induce tissue ablation through thermal effects.

The effect of the electroporation parameters is primarily on the cell membrane and their utility is in permeabilizing the cell membrane for various applications. Electrical parameters that only affect the interior of the cell, without affecting the cell membrane were also identified recently. They are normally referred to as "nanosecond pulses". It has been shown that high amplitude, and short (substantially shorter than electroporation pulses—nanoseconds versus millisecond) length pulses can affect the interior of the cell and in particular the nucleus without affecting the membrane. Studies on nanosecond pulses show that they are "distinctly different than electroporation pulses" (Beebe S J. Fox P M. Rec I J. Somers K. Stark R H. Schoenbach K H. *Nanosecond pulsed electric field (nsPEF) effects on cells and tissues: apoptosis induction and tumor growth inhibition*. PPPS-2001 Pulsed Power Plasma Science 2001. 28th IEEE International Conference on Plasma Science and 13th IEEE International Pulsed Power Conference. Digest of Technical Papers (Cat.

No. 01CH37251). IEEE. Part vol. 1, 2001, pp. 211-15 vol. 1. Piscataway, N.J., USA. Several applications have been identified for nano-second pulses. One of them is for tissue ablation through an effect on the nucleus (Schoenbach, K. H., Beebe, S. J., Buescher, K. S. *Method and apparatus for intracellular electro-manipulation* U.S. Patent Application Pub No. U.S. 2002/0010491 A1, Jan. 24 2002). Another is to regulate genes in the cell interior, (Gunderson, M. A. et al. *Method for intracellular modification within living cells using pulsed electrical fields—regulate gene transcription and entering intracellular* U.S. patent application 2003/0170898 A1, Sep. 11, 2003). Electrical pulses that produce intracellular effects are distinctly different from the pulses which produce electroporation. The distinction can be recognizing through their effect on cells and their utility. The effect of the intracellular electrical pulses is primarily on the intracellular contents of the cell and their utility is in manipulating the intracellular contents for various uses—including ablation. The effect of the electroporation parameters is primarily on the cell membrane and their utility is in permeabilizing the cell membrane for various applications, which will be discussed in greater detail later.

Electroporation is known for over half a century. It was found that as a function of the electrical parameters, electroporation pulses can have two different effects on the permeability of the cell membrane. The permeabilization of the membrane can be reversible or irreversible as a function of the electrical parameters used. In reversible electroporation the cell membrane reseals a certain time after the pulses cease and the cell survives. In irreversible electroporation the cell membrane does not reseal and the cell lyses. A schematic diagram showing the effect of electrical parameters on the cell membrane permeabilization (electroporation) and the separation between: no effect, reversible electroporation and irreversible electroporation is shown in FIG. 1 (Dev, S. B., Rabussay, D. P., Widera, G., Hofmann, G. A., *Medical applications of electroporation*, IEEE Transactions of Plasma Science, Vol 28 No 1, February 2000, pp 206-223) Dielectric breakdown of the cell membrane due to an induced electric field, irreversible electroporation, was first observed in the early 1970s (Neumann, E. and K. Rosenheck, *Permeability changes induced by electric impulses in vesicular membranes*. J. Membrane Biol., 1972. 10: p. 279-290; Crowley, J. M., *Electrical breakdown of biomolecular lipid membranes as an electromechanical instability*. Biophysical Journal, 1973. 13: p. 711-724; Zimmermann, U., J. Vienken, and G. Pilwat, *Dielectric breakdown of cell membranes*, Biophysical Journal, 1974. 14(11): p. 881-899). The ability of the membrane to reseal, reversible electroporation, was discovered separately during the late 1970s (Kinosita Jr, K. and T. Y. Tsong, *Hemolysis of human erythrocytes by a transient electric field*. Proc. Natl. Acad. Sci. USA, 1977. 74(5): p. 1923-1927; Baker, P. F. and D. E. Knight, *Calcium-dependent exocytosis in bovine adrenal medullary cells with leaky plasma membranes*. Nature, 1978. 276: p. 620-622; Gauger, B. and F. W. Bentrup, *A Study of Dielectric Membrane Breakdown in the Fucus Egg*. J. Membrane Biol., 1979. 48(3): p. 249-264).

The mechanism of electroporation is not yet fully understood. It is thought that the electrical field changes the electrochemical potential around a cell membrane and induces instabilities in the polarized cell membrane lipid bilayer. The unstable membrane then alters its shape forming aqueous pathways that possibly are nano-scale pores through the membrane, hence the term "electroporation" (Chang, D. C., et al., *Guide to Electroporation and Electrofusion*. 1992, San Diego, Calif.: Academic Press, Inc.). Mass transfer can now occur through these channels under electrochemical control. Whatever the mechanism through which the cell membrane becomes permeabilized, electroporation has become an important method for enhanced mass transfer across the cell membrane.

The first important application of the cell membrane permeabilizing properties of electroporation is due to Neumann (Neumann, E., et al., *Gene transfer into mouse lyoma cells by electroporation in high electric fields*. J. EMBO, 1982. 1: p. 841-5). He has shown that by applying reversible electroporation to cells it is possible to sufficiently permeabilize the cell membrane so that genes, which are macromolecules that normally are too large to enter cells, can after electroporation enter the cell. Using reversible electroporation electrical parameters is crucial to the success of the procedure, since the goal of the procedure is to have a viable cell that incorporates the gene.

Following this discovery electroporation became commonly used to reversible permeabilize the cell membrane for various applications in medicine and biotechnology to introduce into cells or to extract from cells chemical species that normally do not pass, or have difficulty passing across the cell membrane, from small molecules such as fluorescent dyes, drugs and radioactive tracers to high molecular weight molecules such as antibodies, enzymes, nucleic acids, IIMW dextrans and DNA. It is important to emphasize that in all these applications electroporation needs to be reversible since the outcome of the mass transport requires for the cells to be alive after the electroporation.

Following work on cells outside the body, reversible electroporation began to be used for permeabilization of cells in tissue. Heller, R., R. Gilbert, and M. J. Jaroszeski, *Clinical applications of electrochemotherapy*. Advanced drug delivery reviews, 1999. 35: p. 119-129. Tissue electroporation is now becoming an increasingly popular minimally invasive surgical technique for introducing small drugs and macromolecules into cells in specific areas of the body. This technique is accomplished by injecting drugs or macromolecules into the affected area and placing electrodes into or around the targeted tissue to generate reversible permeabilizing electric field in the tissue, thereby introducing the drugs or macromolecules into the cells of the affected area (Mir, L. M., *Therapeutic perspectives of in vivo cell electropermeabilization*. Bioelectrochemistry, 2001. 53: p. 1-10).

The use of electroporation to ablate undesirable tissue was introduced by Okino and Mohri in 1987 and Mir et al. in 1991. They have recognized that there are drugs for treatment of cancer, such as bleomycin and cys-platinum, which are very effective in ablation of cancer cells but have difficulties penetrating the cell membrane. Furthermore, some of these drugs, such as bleomycin, have the ability to selectively affect cancerous cells which reproduce without affecting normal cells that do not reproduce. Okino and Mori and Mir et al. separately discovered that combining the electric pulses with an impermeant anticancer drug greatly enhanced the effectiveness of the treatment with that drug (Okino, M. and H. Mohri, *Effects of a high-voltage electrical impulse and an anticancer drug on in vivo growing tumors*. Japanese Journal of Cancer Research, 1987. 78(12): p. 1319-21; Mir, L. M., et al., *Electrochemotherapy potentiation of antitumour effect of bleomycin by local electric pulses*. European Journal of Cancer, 1991. 27: p. 68-72). Mir et al. soon followed with clinical trials that have shown promising results and coined the treatment electrochemotherapy (Mir, L. M., et al., *Electrochemotherapy, a novel antitumor treatment: first clinical trial*. C. R. Acad. Sci., 1991. Ser. III 313(613-8)).

Currently, the primary therapeutic in vivo applications of electroporation are antitumor electrochemotherapy (ECT), which combines a cytotoxic nonpermeant drug with permeabilizing electric pulses and electrogenetherapy (EGT) as a form of non-viral gene therapy, and transdermal drug delivery (Mir, L. M., *Therapeutic perspectives of in vivo cell electropermeabilization*. Bioelectrochemistry, 2001. 53: p. 1-10). The studies on electrochemotherapy and electrogenetherapy have been recently summarized in several publications (Jaroszeski, M. J., et al., *In vivo gene delivery by electroporation*. Advanced applications of electrochemistry, 1999. 35: p. 131-137; Heller, R., R. Gilbert, and M. J. Jaroszeski, *Clinical applications of electrochemotherapy*. Advanced drug delivery reviews, 1999. 35: p. 119-129; Mir, L. M., *Therapeutic perspectives of in vivo cell electropermeabilization*. Bioelectrochemistry, 2001. 53: p. 1-10; Davalos, R. V., *Real Time Imaging for Molecular Medicine through electrical Impedance Tomography of Electroporation, in Mechanical Engineering*. 2002, University of California at Berkeley: Berkeley. p. 237). A recent article summarized the results from clinical trials performed in five cancer research centers. Basal cell carcinoma (32), malignant melanoma (142), adenocarcinoma (30) and head and neck squamous cell carcinoma (87) were treated for a total of 291 tumors (Mir, L. M., et al., *Effective treatment of cutaneous and subcutaneous malignant tumours by electrochemotherapy*. British Journal of Cancer, 1998. 77(12): p. 2336-2342).

Electrochemotherapy is a promising minimally invasive surgical technique to locally ablate tissue and treat tumors regardless of their histological type with minimal adverse side effects and a high response rate (Dev, S. B., et al., *Medical Applications of Electroporation*. IEEE Transactions on Plasma Science, 2000. 28(1): p. 206-223; Heller, R., R. Gilbert, and M. J. Jaroszeski, *Clinical applications of electrochemotherapy*. Advanced drug delivery reviews, 1999. 35: p. 119-129). Electrochemotherapy, which is performed through the insertion of electrodes into the undesirable tissue, the injection of cytotoxic dugs in the tissue and the application of reversible electroporation parameters, benefits from the ease of application of both high temperature treatment therapies and non-selective chemical therapies and results in outcomes comparable of both high temperature therapies and non-selective chemical therapies.

In addition, because the cell membrane permeabilization electrical field is not affected by the local blood flow, the control over the extent of the affected tissue by this mode of ablation does not depend on the blood flow as in thermal and non-selective chemical therapies. In designing electroporation protocols for ablation of tissue with drugs that are incorporated in the cell and function in the living cells it was important to employ reversible electroporation; because the drugs can only function in a living cell. Therefore, in designing protocols for electrochemotherapy the emphasis was on avoiding irreversible electroporation. The focus of the entire field of electroporation for ablation of tissue was on using reversible pulses, while avoiding irreversible electroporation pulses, that can cause the incorporation of selective drugs in undesirable tissue to selectively destroy malignant cells. Electrochemotherapy which employs reversible electroporation in combination with drugs, is beneficial due to its selectivity however, a disadvantage is that by its nature, it requires the combination of chemical agents with an electrical field and it depends on the successful incorporation of the chemical agent inside the cell.

The present inventors have recognized that irreversible electroporation, whose ability to lyse various types of cells outside the body has been known for at least five decades, has never been used for tissue ablation in the body and in fact was considered detrimental to conventional electrochemotherapy. Although irreversible electroporation of tissue is not as selective as reversible electroporation with drug incorporation the present inventors have found it to be effective in ablating volumes of undesirable tissues in a way comparable to other non-discriminating bulk ablative methods such as cryosurgery, thermal methods or alcohol injection.

SUMMARY OF THE INVENTION

The present invention comprises a method for the ablation of undesirable tissue, involving the placement of electrodes into or near the vicinity of the undesirable tissue with the application of electrical pulses causing irreversible electroporation of the cells throughout the entire undesirable region. The electric pulses irreversibly permeate the membranes, thereby invoking cell death. The length of time of the electrical pulses, the voltage applied and the resulting membrane permeability are all controlled within defined ranges. The irreversibly permeabilized cells may be left in situ and may be removed by natural processes such as the body's own immune system. The amount of tissue ablation achievable through the use of irreversible electroporation without inducing thermal damage is considerable, as disclosed and described here.

This concept of irreversible electroporation in tissue to destroy undesirable tissues is different from other forms of electrical therapies and treatments. Irreversible electroporation is different from intracellular electro-manipulation which substantially only affects the interior of the cell and does not cause irreversible cell membrane damage. Irreversible electroporation is not electrically induced thermal coagulation—which induces cell damage through thermal effects but rather a more benign method to destroy only the cell membrane of cells in the targeted tissue. Irreversible electroporation which irreversible destroys the cell membrane is also different from electrochemotherapy in which reversible electroporation pulses are used to introduce drugs into the living cells and in which the drugs subsequently affect the living cell.

An electrical pulse can either have no effect on the cell membrane, effect internal cell components, reversibly open the cell membrane after which cells can survive, or irreversibly open the cell membrane, after which the cells die. Of these effects, irreversible electroporation of tissue was (prior to present invention) generally considered undesirable due to the possibility of instantaneous necrosis of the entire tissue affected by the electrical field, regardless of its diseased or healthy state. Irreversible electroporation is detrimental in certain applications, such as gene therapy or electrochemotherapy, where the sole purpose of the electric pulses is to facilitate the introduction of the drug or gene into the cells of a tissue without killing the cell (Mir., L. M. and S. Orlowski, *The basis of electrochemotherapy, in Electrochemotherapy, electrogenetherapy, and transdermal drug delivery: Electrically mediated delivery of molecules to cells*, M. J. Jaroszeski, R. Heller, R. Gilbert, Editors, 2000, Humana Press, p. 99-118).

In contrast, irreversible electroporation of the type described here, solely uses electrical pulses to serve as the active means for tissue destruction by a specific means, i.e. by fatally disrupting the cell membrane. Electrochemotherapy may be selective, but it does require the combination of chemical agents with the electrical field. Irreversible electroporation, although non-selective, may be used for the ablation of undesirable tissue (such as a tumor) as a minimally invasive surgical procedure without the use of adjuvant drugs. Its non-selective mode of tissue ablation is acceptable in the field of minimally invasive surgery and provides results which in some ways are comparable to cryosurgery, non-selective chemical ablation and high temperature thermal ablation.

An aspect of the invention is a method whereby cells of tissue are irreversibly electroporated by applying pulses of very precisely determined length and voltage. This may be done while measuring and/or observing changes in electrical impedance in real time and noting decreases at the onset of electroporation and adjusting the current in real time to obtain irreversible cellular damage without thermal damage. In embodiments where voltage is applied, the monitoring of the impedance affords the user knowledge of the presence or absence of pores. This measurement shows the progress of the pore formation and indicates whether irreversible pore formation, leading to cell death, has occurred.

An aspect of this invention is that the onset and extent of electroporation of cells in tissue can be correlated to changes in the electrical impedance (which term is used herein to mean the voltage over current) of the tissue. At a given point, the electroporation becomes irreversible. A decrease in the resistivity of a group of biological cells occurs when membranes of the cells become permeable due to pore formation. By monitoring the impedance of the biological cells in a tissue, one can detect the average point in time in which pore formation of the cells occurs, as well as the relative degree of cell membrane permeability due to the pore formation. By gradually increasing voltage and testing cells in a given tissue one can determine a point where irreversible electroporation occurs. This information can then be used to establish that, on average, the cells of the tissue have, in fact, undergone irreversible electroporation. This information can also be used to control the electroporation process by governing the selection of the voltage magnitude.

The invention provides the simultaneous irreversible electroporation of multitudes of cells providing a direct indication of the actual occurrence of electroporation and an indication of the degree of electroporation averaged over the multitude. The discovery is likewise useful in the irreversible electroporation of biological tissue (masses of biological cells with contiguous membranes) for the same reasons. The benefits of this process include a high level of control over the beginning point of irreversible electroporation.

A feature of the invention is that the magnitude of electrical current during electroporation of the tissue becomes dependent on the degree of electroporation so that current and pulse length are adjusted within a range predetermined to obtain irreversible electroporation of targeted cells of the tissue while minimizing cellular damage to surrounding cells and tissue.

An aspect of the invention is that pulse length and current are precisely adjusted within ranges to provide more than mere intracellular eleccto-manipulation which results in cell death and less than that which would cause thermal damages to the surrounding tissues.

Another aspect of the invention is that the electroporation is carried out without adding drugs, DNA, or other materials of any sort to be brought into the cells.

Another feature of the invention is that measuring current (in real time) through a circuit gives a measurement of the average overall degree of electroporation obtained.

Another aspect of the invention is that the precise electrical resistance of the tissue is calculated from cross-time voltage measurement with probe electrodes and cross-current measurement with the circuit attached to electroporation electrodes.

Another aspect of the invention is that the precise electrical resistance of the tissue is calculated from cross-time voltage measurement with probe electrodes and cross-current measurement with the circuit attached to electroporation electrodes.

Another aspect of the invention is that electrical measurements of the tissue can be used to map the electroporation distribution of the tissue.

Unlike electrical impedance tomography for detection of reversible electroporation which needs to be done during or close to the time the reversible electroporation pulses are applied—because of the transient nature of the reversible electroporation; in irreversible electroporation it is possible and perhaps even preferential to perform the current or EIT measurements a substantial time (several minutes or more) after the electroporation to verify that it is indeed irreversible.

These and further features, advantages and objects of the invention will be better understood from the description that follows.

BRIEF DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIGS. 4A, 4B and 4C are images showing the effect of electrode diameter for a 4-electrode configuration with 10 mm spacing wherein FIG. 4A is for 0.5 mm diameter and 940V; FIG. 4B is for 1.0 mm diameter and 1404V and FIG. 4C is for 1.5 mm and 1685V.

FIG. 5A shows results with a 5 mm and 910V; FIG. 5B 7.5 mm and 1175V and FIG. 5C 10 mm and 1404V.

FIG. 7 is an image showing reversible electroporation with 1 mm electrodes, 10 mm spacing. A voltage of 189V applied between the electrodes induces reversible electroporation without any irreversible electroporation by not surpassing the 680 V/cm irreversible electroporation threshold anyone in the domain. The shaded area is greater than 360 V/cm.

FIG. 8A no blood flow or metabolism. FIG. 8B $w_b$=1 kg/m$^3$, $c_b$=3640 J/(kg K), $T_b$=37° C., and q'''=33.8 kW/m$^3$.

DETAILED DESCRIPTION OF THE INVENTION

Figure 1:
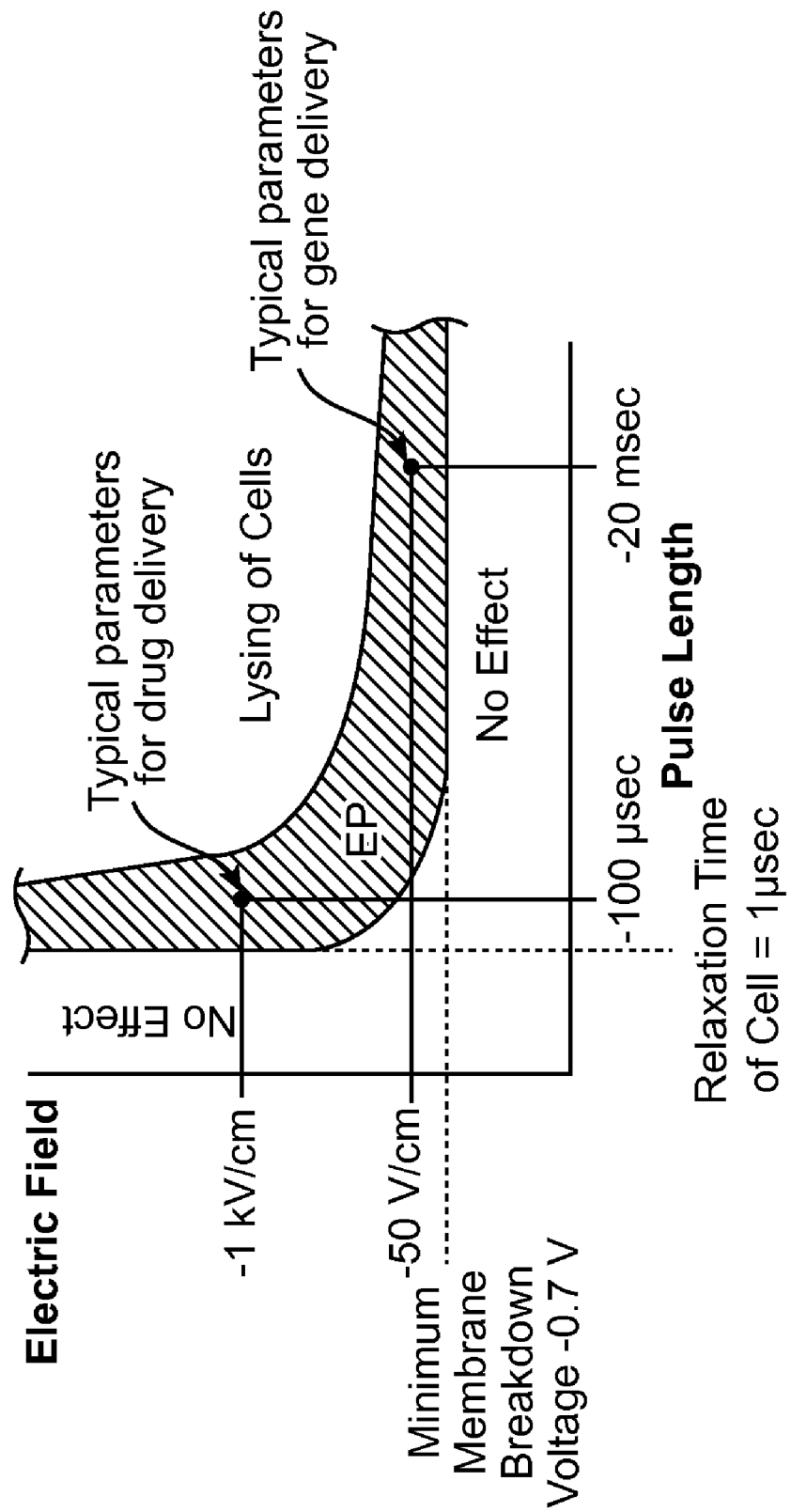
FIG. 1. is a graph showing a schematic relationship between field strength and pulselength applicable to the electroporation of cells.

Before the present methods, treatments and devices are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

It must be noted that as used herein and in the appended claims, the singular forms "a", "an", and "the" include plural referents unless the context clearly dictates otherwise. Thus, for example, reference to "a pulse" includes a plurality of such pulses and reference to "the sample" includes reference to one or more samples and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "reversible electroporation" encompasses permeabilization of the cell membrane through the application of electrical pulses across the cell. In "reversible electroporation" the permeabilization of the cell membrane ceases after the application of the pulse and the cell membrane permeability reverts to normal. The cell survives "reversible electroporation." It is used as a means for introducing chemicals, DNA, or other materials into cells.

The term "irreversible electroporation" also encompasses the permeabilization of the cell membrane through the application of electrical pulses across the cell. However, in "irreversible electroporation" the permeabilization of the cell membrane does not cease after the application of the pulse and the cell membrane permeability does not revert to normal. The cell does not survive "irreversible electroporation" and the cell death is caused by the disruption of the cell membrane and not merely by internal perturbation of cellular components. Openings in the cell membrane are created and/or expanded in size resulting in a fatal disruption in the normal controlled flow of material across the cell membrane. The cell membrane is highly specialized in its ability to regulate what leaves and enters the cell. Irreversible electroporation destroys that ability to regulate in a manner such that the cell can not compensate and as such the cell dies.

INVENTION IN GENERAL

The invention provides a method and a system for destruction (ablation) of undesirable tissue. It involves the insertion (bringing) electroporation electrodes to the vicinity of the undesirable tissue and in good electrical contact with the tissue and the application of electrical pulses that cause irreversible electroporation of the cells throughout the entire area of the undesirable tissue. The cells whose membrane was irreversible permeabilized may be left in situ (not removed) and as such may be gradually removed by the body's immune system. Cell death is produced by inducing the electrical parameters of irreversible electroporation in the undesirable area.

Electroporation protocols involve the generation of electrical fields in tissue and are affected by the Joule heating of the electrical pulses. When designing tissue electroporation protocols it is important to determine the appropriate electrical parameters that will maximize tissue permeabilization without inducing deleterious thermal effects. It has been shown that substantial volumes of tissue can be electroporated with reversible electroporation without inducing damaging thermal effects to cells and has quantified these volumes (Davalos, R. V., B. Rubinsky, and L. M. Mir, *Theoretical analysis of the thermal effects during in vivo tissue electroporation*. Bioelectrochemistry, 2003. Vol. 61(1-2): p. 99-107).

The electrical pulses required to induce irreversible electroporation in tissue are larger in magnitude and duration from the electrical pulses required for reversible electroporation. Further, the duration and strength of the pulses required for irreversible electroporation are different from other methodologies using electrical pulses such as for intracellular electro-manipulation or thermal ablation. The methods are very different even when the intracellular (nano-seconds) electro-manipulation is used to cause cell death, e.g. ablate the tissue of a tumor or when the thermal effects produce damage to cells causing cell death.

Typical values for pulse length for irreversible electroporation are in a range of from about 5 microseconds to about 62,000 milliseconds or about 75 microseconds to about 20,000 milliseconds or about 100 microseconds±10 microseconds. This is significantly longer than the pulse length generally used in intracellular (nano-seconds) electro-manipulation which is 1 microsecond or less—see published U.S. application 2002/0010491 published Jan. 24, 2002.

The pulse is at voltage of about 100 V/cm to 7,000 V/cm or 200 V/cm to 2000 V/cn or 300 V/cm to 1000 V/cm about 600 V/cm±10% for irreversible electroporation. This is substantially lower than that used for intracellular electro-manipulation which is about 10,000 V/cm, see U.S. application 2002/0010491 published Jan. 24, 2002.

The voltage expressed above is the voltage gradient (voltage per centimeter). The electrodes may be different shapes and sizes and be positioned at different distances from each other. The shape may be circular, oval, square, rectangular or irregular etc. The distance of one electrode to another may be 0.5 to 10 cm., 1 to 5 cm., or 2-3 cm. The electrode may have a surface area of 0.1-5 sq. cm. or 1-2 sq. cm.

The size, shape and distances of the electrodes can vary and such can change the voltage and pulse duration used. Those skilled in the art will adjust the parameters in accordance with this disclosure to obtain the desired degree of electroporation and avoid thermal damage to surrounding cells.

Thermal effects require electrical pulses that are substantially longer from those used in irreversible electroporation (Davalos, R. V., B. Rubinsky, and L. M. Mir, *Theoretical analysis of the thermal effects during in vivo tissue electroporation*. Bioelectrochemistry, 2003. Vol. 61(1-2): p. 99-107). FIG. 1 is showing that irreversible electroporation pulses are longer and have higher amplitude than the reversible electroporation pulses. When using irreversible electroporation for tissue ablation, there may be concern that the irreversible electroporation pulses will be as large as to cause thermal damaging effects to the surrounding tissue and the extent of the tissue ablated by irreversible electroporation will not be significant relative to that ablated by thermal effects. Under such circumstances irreversible electroporation could not be considered as an effective tissue ablation modality as it will act in superposition with thermal ablation.

The present invention evaluates, through mathematical models and experiment, the maximal extent of tissue ablation that could be accomplished by irreversible electroporation prior to the onset of thermal effects. The models focused on electroporation of liver tissue with two and four needle electrodes and on electroporation of liver tissue with two infinite parallel plates using available experimental data. The experiment (EXAMPLE 3) evaluates irreversible electroporation between two cylindrical electrodes, also in the liver. The liver was chosen because it is considered a potential candidate for irreversible electroporation ablation. The results show that the area that can be ablated by irreversible electroporation prior to the onset of thermal effects is comparable to that which can be ablated by electrochemotherapy, validating the use of irreversible electroporation as a potential minimally invasive surgical modality.

Earlier studies have shown that the extent of electroporation can be imaged in real time with electrical impedance tomography (EIT) (Davalos, R. V., B. Rubinsky, and D. M. Otten, *A feasibility study for electrical impedance tomography as a means to monitor tissue electroporation for molecular medicine*. IEEE Transactions on Biomedical Engineering, 2002. 49(4): p. 400-403). In irreversible electroporation the electroporated area persists indefinitely after the electroporation pulse, showing that irreversible electroporation may be imaged leisurely with EIT. Irreversible electroporation, therefore, has the advantage of a tissue ablation technique that is as easy to apply as high temperature ablation, without the need for adjuvant chemicals as electrochemotherapy and with real-time control of the affected area with electrical impedance tomography.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The mathematical model provided here shows that irreversible tissue ablation can affect substantial volumes of tissue, without inducing damaging thermal effects. To this end, the present invention uses the Laplace equation to calculate the electrical potential distribution in tissue during typical electroporation pulses and a modified Pennes (bioheat), (Pennes, H. H., *Analysis of tissue and arterial blood flow temperatures in the resting forearm*. J of Appl. Physiology., 1948. 1: p. 93-122), equation to calculate the resulting temperature distribution. It is important to note that there are several forms of the bioheat equation which have been reviewed (Carney, C. K., *Mathematical models of bioheat transfer*, in *Bioengineering heat transfer*, Y. I. Choi, Editor. 1992, Academic Press, Inc: Boston. p. 19-152; Eto, T. K. and B. Rubinsky, *Bioheat transfer*, in *Introduction to bioengineering*, S. A. Berger, W. Goldsmith, and E. R. Lewis, Editors. 1996, Oxford Press). While the Pennes equation is controversial, it is nevertheless commonly used because it can provide an estimate of the various biological heat transfer parameters, such as blood flow and metabolism. The modified Pennes equation in this study contains the Joule heating term in tissue as an additional heat source.

The electrical potential associated with an electroporation pulse is determined by solving the Laplace equation for the potential distribution:

$$\nabla \cdot (\sigma \nabla \phi) = 0 \quad (1)$$

where $\phi$ is the electrical potential and $\sigma$ is the electrical conductivity. The electrical boundary condition of the tissue that is in contact with the leftmost electrode(s) on which the electroporation pulse is applied is:

$$\phi = V_0 \quad (2)$$

The electrical boundary condition at the interface of the rightmost electrode(s) is:

$$\phi = 0 \quad (3)$$

The boundaries where the analyzed domain is not in contact with an electrode are treated as electrically insulative to provide an upper limit to the electrical field near the electroporation electrodes and an upper limit to the temperature distribution that results from electroporation:

$$\frac{\partial \phi}{\partial n} = 0 \quad (4)$$

Solving the Laplace equation enables one to calculate the associated Joule heating, the heat generation rate per unit volume from an electrical field (p):

$$p = \sigma |\nabla \phi|^2 \quad (5)$$

This term is added to the original Pennes equation, (Pennes, H. H., *Analysis of tissue and arterial blood flow temperatures in the resting forearm*. J of Appl. Physiology., 1948. 1: p. 93-122) to represent the heat generated from the electroporation procedure:

$$\nabla \cdot (k \nabla T) + w_b c_b (T_a - T) + q''' + p = \rho c_p \frac{\partial T}{\partial t} \quad (6)$$

To solve equation (4) it is assumed that the entire tissue is initially at the physiological temperature of 37° C.:

$$T(x,y,z,0) = 37 \quad (7)$$

The outer surface of the analyzed domain and the surfaces of the electrodes are taken to be adiabatic, which should produce an upper limit to the calculated temperature distribution in the tissue:

$$\frac{\partial T}{\partial n} = 0 \text{ on the electrodes boundary and the outer surface domain} \quad (8)$$

The analysis modeled conditions typical to tissue electroporation in the liver. The liver was chosen because it is the organ that most minimally invasive ablation techniques treat since cancer in the liver can be resolved by extirpation of the diseased area while surgical resection is not possible in many cases for this organ (Onik, G., B. Rubinsky, and et al., *Ultrasound-Guided Hepatic Cryosurgery in the Treatment of Metastatic Colon Carcinoma*. Cancer, 1991. 67(4): p. 901-907). The electroporation parameters, i.e. pulse parameters for reversible and irreversible electroporation where obtained from rat liver data (Miklavcic, D., et al., *A validated model of in vivo electric field distribution in tissues for electrochemotherapy and for DNA electrotransfer for gene therapy*. Biochimica et Biophysica Acta, 2000. 1523(1): p. 73-83; Suzuki, T., et al., *Direct gene transfer into rat liver cells by in vivo electroporation*. FEBS Letters, 1998. 425(3): p. 436-440), but biological parameters corresponding to the human liver were used in the analysis. Tissue thermal properties are taken from reference (Duck, F. A., *Physical Properties of Tissues: A Comprehensive Reference Book*. 1990, San Diego: Academic Press) and the electrical properties from reference (Boone, K., D. Barber, and B. Brown, *Review-Imaging with electricity: report of the European Concerted Action on Impedance Tomography*. J. Med. Eng. Technol., 1997. 21: p. 201-232) and are listed in table 1. The tissue is assumed isotropic and macroscopically homogeneous. The intent of the analysis was to determine the extent of the region in which reversible or irreversible electroporation is induced in the liver for various electroporation voltages and durations while the maximal temperature in the tissue is below 50° C. Thermal damage is a time-dependent process described by an Arrhenius type equation (Henriques, F. C. and A. R. Moritz, *Studies in thermal injuries: the predictability and the significance of thermally induced rate processes leading to irreversible epidermal damage*. Arch Pathol., 1947. 43: p. 489-502; Diller, K. R., *Modeling of bioheat transfer processes at high and low temperatures*, in *Bioengineering heat transfer*, Y. I. Choi, Editor. 1992, Academic Press, Inc: Boston. p. 157-357), $$\Omega = \int \xi e^{-E_a/RT} dt \quad (9)$$

Where $\Omega$ is a measure of thermal damage, $\xi$ is the frequency factor, $E_\alpha$ is the activation energy and R is the universal gas constant. A detailed description on the various degrees of thermal damage as described in Equation (9) above can be found in (Diller, K. R., *Modeling of bioheat transfer processes at high and low temperatures*, in *Bioengineering heat transfer*, Y. I. Choi, Editor. 1992, Academic Press, Inc: Boston. p. 157-357).

A careful examination shows that the thermal damage is a complex function of time, temperature and all the parameters in Equation (9) above and that there are various degrees of thermal damage. In various applications or for various considerations it is possible to design irreversible electroporation protocols that induce some degree of thermal damage, either in part of the electroporated region or at a reduced level throughout the electroporated region. However, in this example we have chosen 50° C. as the target temperature for several reasons. Thermal damage begins at temperatures higher than 42° C., but only for prolonged exposures. Damage is relatively low until 50° C. to 60° C. at which the rate of damage dramatically increases (Diller, K. R., *Modeling of bioheat transfer processes at high and low temperatures*, in *Bioengineering heat transfer*, Y. I. Choi, Editor. 1992, Academic Press, Inc: Boston. p. 157-357). Therefore 50 C will be a relatively low bound on the possible thermal effects during irreversible electroporation. It is anticipated that the electrical parameters chosen for irreversible electroporation without a thermal effect could be substantially longer and higher than those obtained from an evaluation for 50 C in this example. Furthermore, since the Laplace and bioheat equations are linear, the results provided here can be extrapolated and considered indicative of the overall thermal behavior.

The analyzed configurations have two needles or four needle electrodes embedded in a square model of the liver. Needle electrodes are commonly used in tissue electroporation and will be most likely also used in the liver (Somiari, S., et al., *Theory and in vivo application of electroporative gene delivery*. Molecular Therapy, 2000. 2(3): p. 178-187). The square model of the liver was chosen large enough to avoid outer surface boundary effects and to produce an upper limit for the temperature, which develops during electroporation in the liver. For each configuration the surface of one electrode is assumed to have a prescribed voltage with the other electrode set to ground. The effect of the spacing between the electrodes was investigated by comparing distances of 5, 7.5 and 10 mm, which are typical. The electrodes were also modeled with typical dimensions of 0.5, 1 and 1.5 mm in diameter. The blood flow perfusion rate was taken to zero or 1.0 kg/m$^3$ s (Deng, Z. S. and J. Liu, *Blood perfusion-based model for characterizing the temperature fluctuations in living tissue*. Phys A STAT Mech Appl, 2001. 300: p. 521-530). The metabolic heat was taken to be either zero or 33.8 kW/m$^3$ (Deng, Z. S. and J. Liu, *Blood perfusion-based model for characterizing the temperature fluctuations in living tissue*. Phys A STAT Mech Appl, 2001. 300: p. 521-530).

The calculations were made for an electroporation pulse of 800 µs. This pulse duration was chosen because typically, reversible electroporation is done with eight separate 100 µs pulses, (Miklavcic, D., et al., *A validated model of in vivo electric field distribution in tissues for electrochemotherapy and for DNA electrotransfer for gene therapy*. Biochimica et Biophysica Acta, 2000. 1523(1): p. 73-83) and therefore the value we chose is an upper limit of the thermal effect in a pulse time frame comparable to that of reversible electroporation. Consequently, the results obtained here are the lower limit in possible lesion size during irreversible electroporation. It should be emphasized that we believe irreversible electroporation tissue ablation can be done with shorter pulses than 800 µs. To evaluate the thermal effect, we gradually increased in our mathematical model the applied pulse amplitude for the 800 µs pulse length until our calculations indicated that the electroporation probe temperature reached 50° C., which we considered to be the thermal damage limit. Then, we evaluated the electric field distribution throughout the liver.

A transmembrane potential on the order of 1V is required to induce irreversible electroporation. This value is dependent on a variety of conditions such as tissue type, cell size and other external conditions and pulse parameters. The primary electrical parameter affecting the transmembrane potential for a specific tissue type is the amplitude of the electric field to which the tissue is exposed. The electric field thresholds used in estimating the extent of the region that was irreversibly electroporated were taken from the fundamental studies of Miklavcic, Mir and their colleagues performed with rabbit liver tissue (Miklavcic, D., et al., *A validated model of in vivo electric field distribution in tissues for electrochemotherapy and for DNA electrotransfer for gene therapy*. Biochimica et Biophysica Acta, 2000. 1523(1): p. 73-83). In this study, that correlated electroporation experiments with mathematical modeling, they have found that the electric field for reversible electroporation is 362+/−21 V/cm and is 637+/−43 V/cm for irreversible electroporation for rat liver tissue. Therefore, in the analysis an electric field of 360 V/cm is taken to represent the delineation between no electroporation and reversible electroporation and 680 V/cm to represent the delineation between reversible and irreversible electroporation.

All calculations were performed using MATLAB's finite element solver, Femlab v2.2 (The MathWorks, Inc. Natick, Mass.). To ensure mesh quality and validity of solution, the mesh was refined until there was less than a 0.5% difference in solution between refinements. The baseline mesh with two 1 mm electrodes, 10 mm spacing had 4035 nodes and 7856 triangles. The simulations were conducted on a Dell Optiplex GX240 with 512 MB of RAM operating on Microsoft Windows 2000.

RESULTS AND DISCUSSION

Figure 2A:
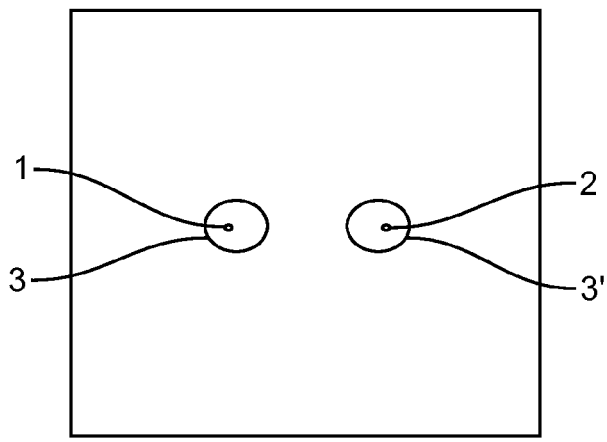
FIGS. 2A, 2B and 2C are each images of irreversibly electroporated areas for two-electrode configurations using 10 mm center-to-center spacing as following for FIGS. 2A, B and C: (2A) 0.5 mm (857V); (2B) 1.0 mm (1295V); (2C) 1.5 mm (1575V) diameter electrodes with a 680 V/cm threshold for irreversible electroporation.
Figure 2B:
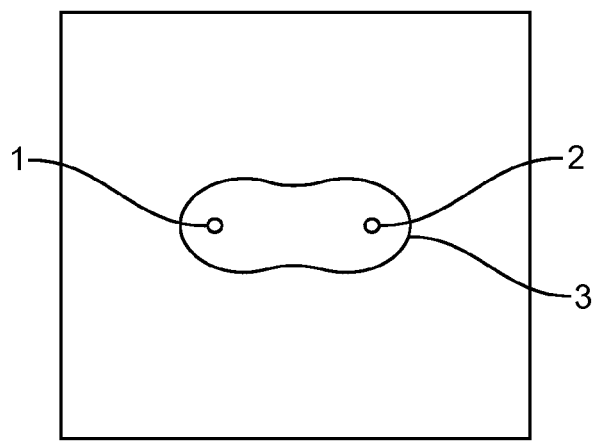
Figure 2C:
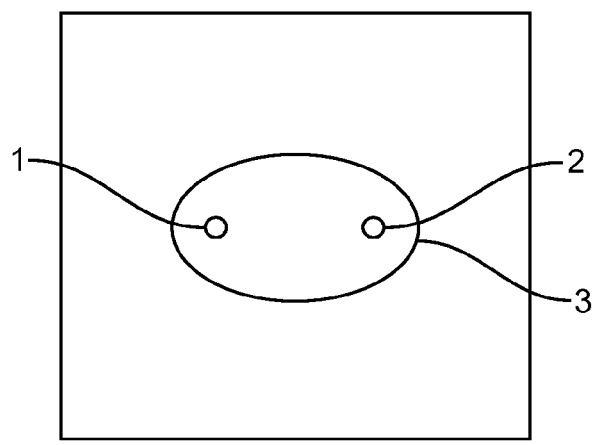
Figure 3A:
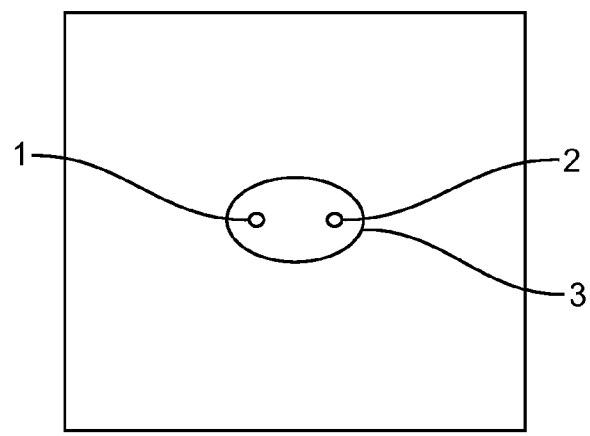
FIGS. 3A, 3B, and 3C are images showing irreversibly electroporated regions using a 680 V/cm threshold for a two-electrode confirmation with 1 mm diameter and 876V and 5 mm spacing for FIG. 3A; 1116V and 7.5 mm for FIG. 3B; and 1295V and 10 mm spacing for FIG. 3C.
Figure 3B:
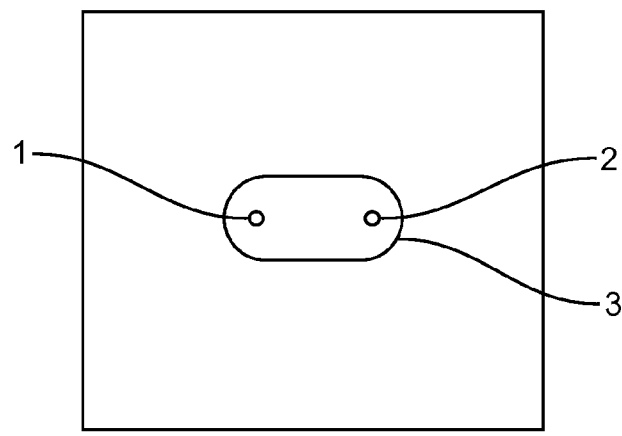
Figure 3C:
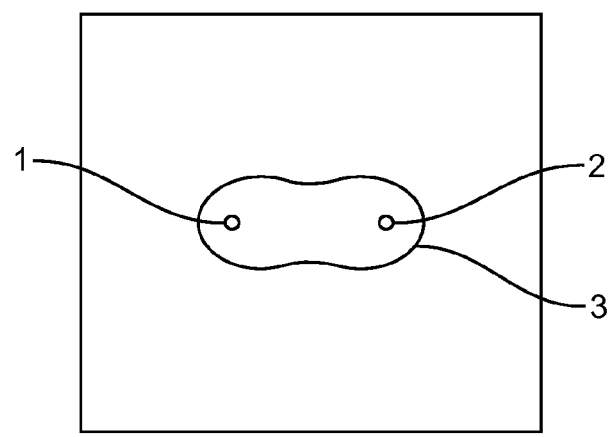

FIGS. 2 and 3 examine the effect of the electrode size and spacing on the ablated area in a two-needle electroporation configuration. In obtaining these figures, we ignored the effect of the blood flow and metabolism in the heat transfer equation, which should give an upper limit for the estimated ablation area. FIG. 2 compares the extent of the irreversible electroporated area for electroporation electrode sizes of 0.5, 1 and 1.5 mm in diameter and a distance between electrodes of 10 mm. The strong effect of the electrode size is evident. It is seen that for the smaller electrodes, the irreversibly electroporated area is not contiguous, while for a 1.5 mm electrode the area of potential tissue, ablation has an elliptical shape with dimensions of about 15 mm by 10 mm. In the brackets, we give the electroporation voltage for which the probe temperature reaches 50° C. in these three configurations. It is seen that the range is from 857V for the 0.5 mm probe to 1575V for the 1.5 mm probe. This is within the typical range of tissue electroporation pulses. FIG. 3 evaluates the effect of the spacing between the electrodes. It is observed that in the tested range, the small dimension of the contiguous elliptical shape of the ablated lesion remains the same, while the larger dimension seems to scale with the distance between the electrodes.

Figure 4A:
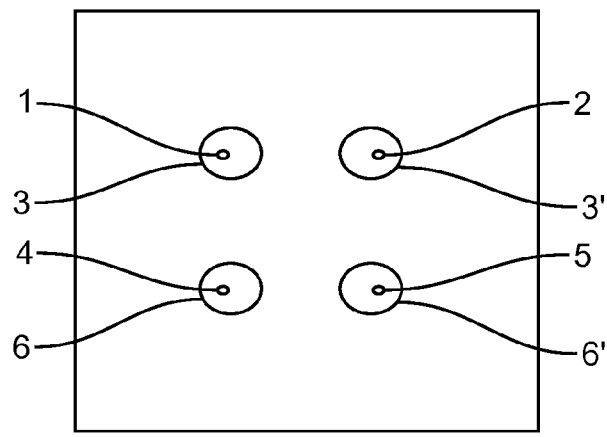
Figure 4B:
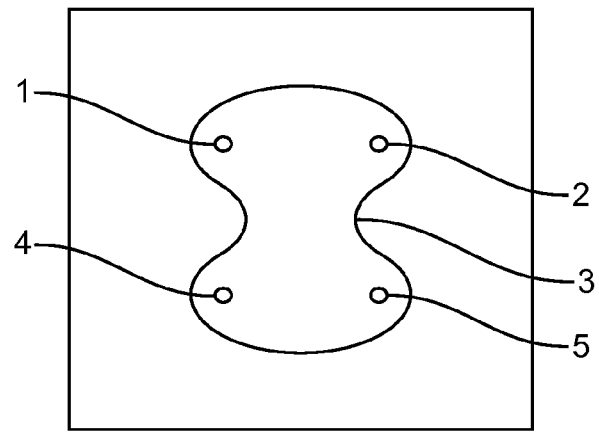
Figure 4C:
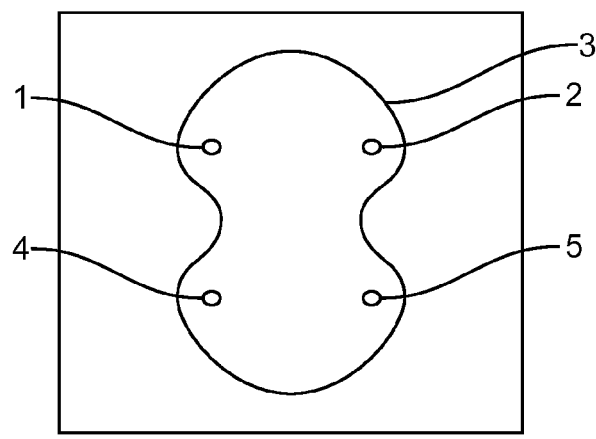
Figure 5A:
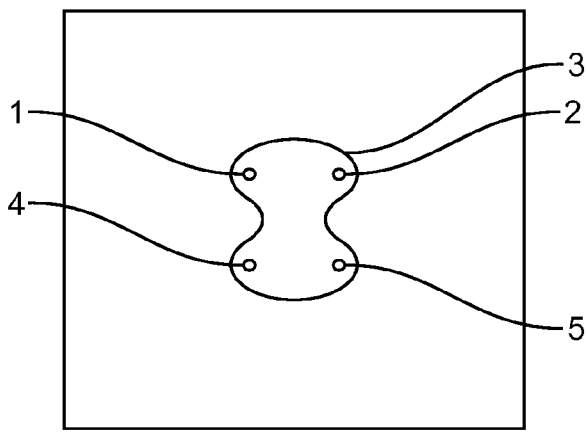
FIGS. 5A, 5B and 5C are images showing the effect of electrode spacing for a 4-electrode configuration wherein the electrode is 1 mm in diameter
Figure 5B:
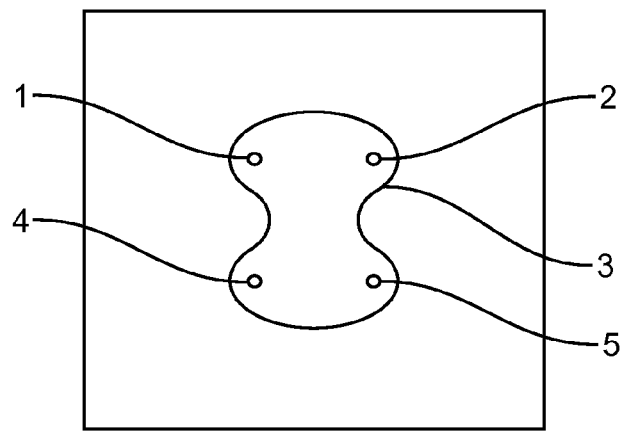
Figure 5C:
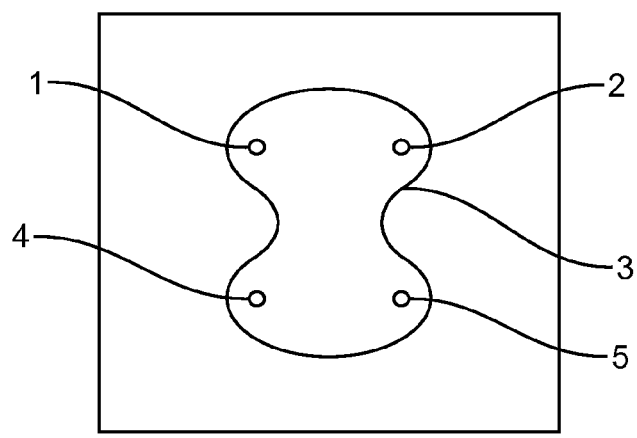

FIGS. 2 and 3 demonstrate that the extent of tissue ablation with irreversible electroporation is comparable to that of other typical minimally invasive methods for tissue ablation, such as cryosurgery (Onik, G. M., B. Rubinsky, and et. al., *Ultrasound-guided hepatic cryosurgery in the treatment of metastatic colon carcinoma*. Cancer, 1991. 67(4): p. 901-907; Onik, G. M., et al., *Transrectal ultrasound-guided percutaneous radical cryosurgical ablation of the prostate*. Cancer, 1993. 72(4): p. 1291-99). It also shows that varying electrode size and spacing can control lesion size and shape. The shape and size of the ablated lesion can be also controlled by varying the number of electrodes used. This is shown in FIGS. 4 and 5, for a four-electrode configuration. These figures also compare the effect of probe size and spacing and the results were also obtained by ignoring the effect of blood flow and metabolism in the energy equation. Again, it is seen that larger electrodes have a substantial effect on the extent of the ablated region and that the extent of ablation scales with the spacing between the electrodes.

Figure 6:
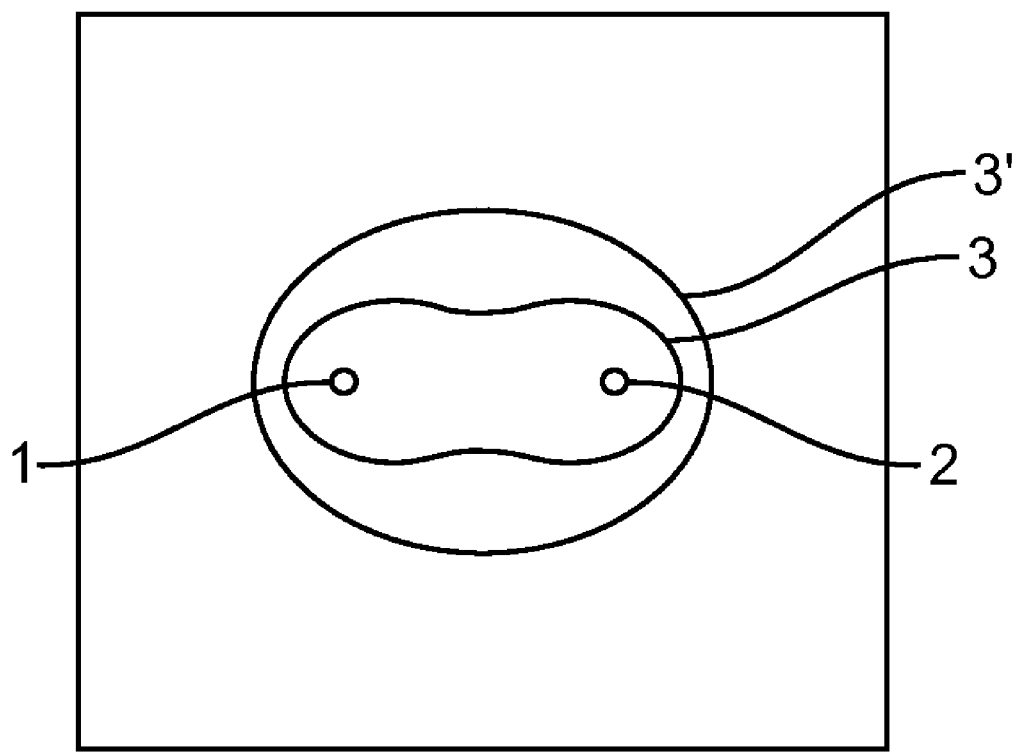
FIG. 6 is an image showing the irreversible (1295V, 680 V/cm threshold) as compared to the reversible region (1300V, 360 V/cm threshold) using virtually the same electrical parameters. 1300V is the most common voltage applied across two electrodes for ECT. The most common voltage parameters are eight 100 µs pulses at a frequency of 1 Hz. Applying a single 800 µs pulse provides a conservative estimate of the heating associated with a procedure. The one second space normally between pulses will enlarge an area amount of heat to be dissipated through the tissue.
Figure 7:
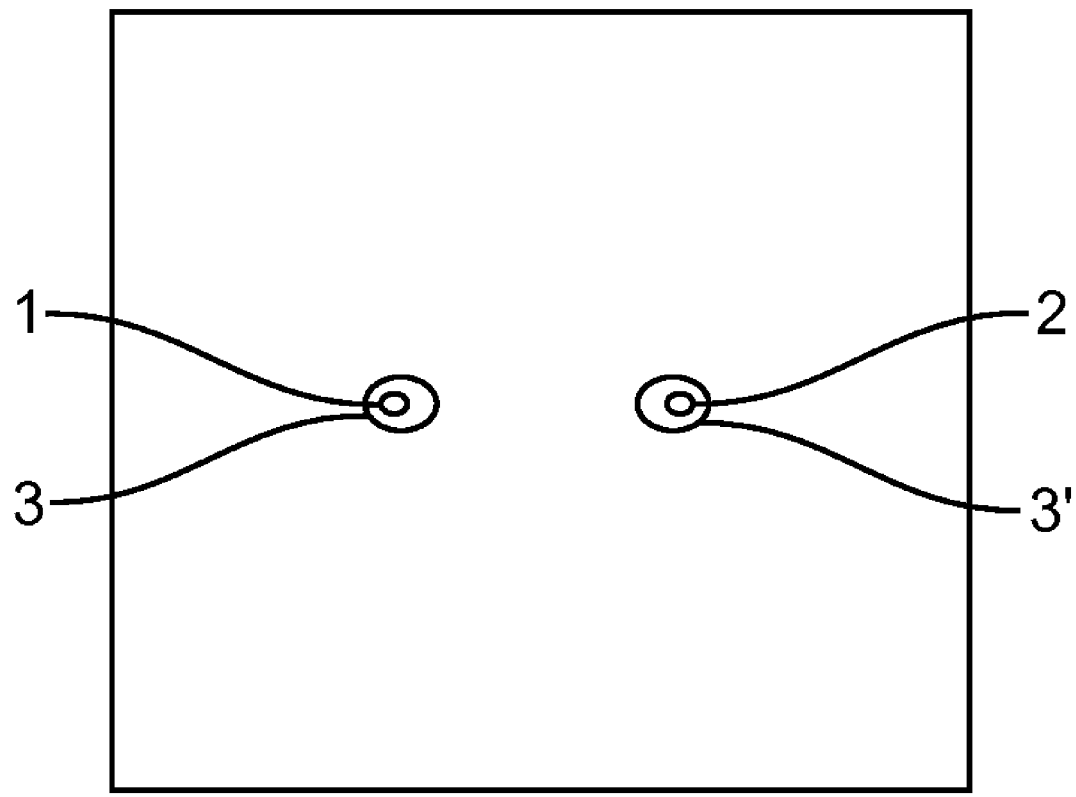

A comparison between reversible and irreversible electroporation protocols can be achieved from FIGS. 6 and 7. In FIG. 6, an 800 µs, 1295 V pulse was applied between two 1.5 mm diameter electrodes placed 10 mm apart. This produces a tissue temperature lower than 50° C. The figure plots the margin of the irreversibly electroporated region, i.e. the 680 V/cm voltage-to-distance gradients and that of the reversible electroporated region, the 360 V/cm gradients. FIG. 7 was obtained for two 1 mm electrodes placed 10 mm apart. In this figure, we produced an electroporated region that was only reversibly electroporated, i.e. with electric fields lower than 360 V/cm. In comparing FIGS. 6 and 7, it is obvious that the extent of the ablated area possible through electrochemotherapy alone is substantially smaller than that through irreversible electroporation alone.

Figure 8A:
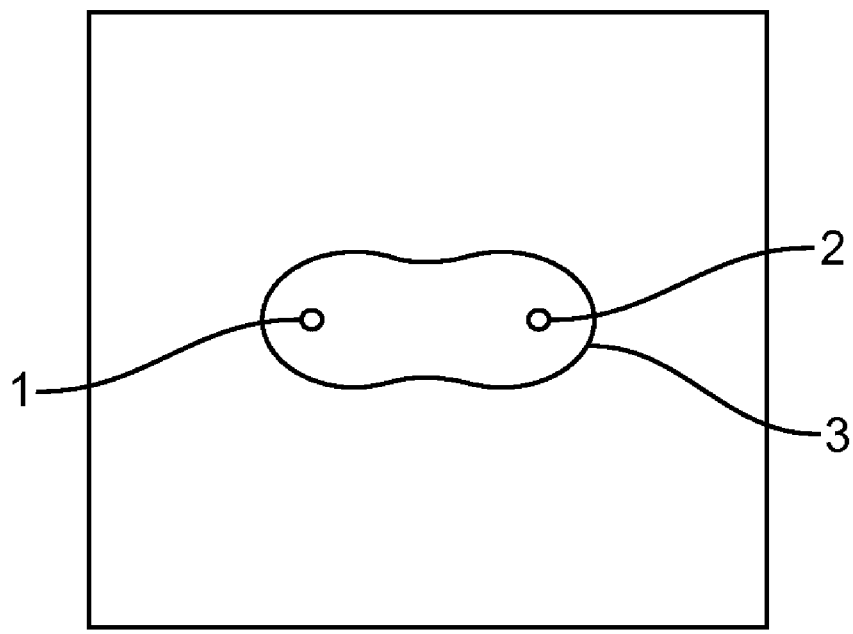
FIGS. 8A and 8B show a comparison of the effect of blood flow and metabolism on the amount of irreversible electroporation.
Figure 8B:
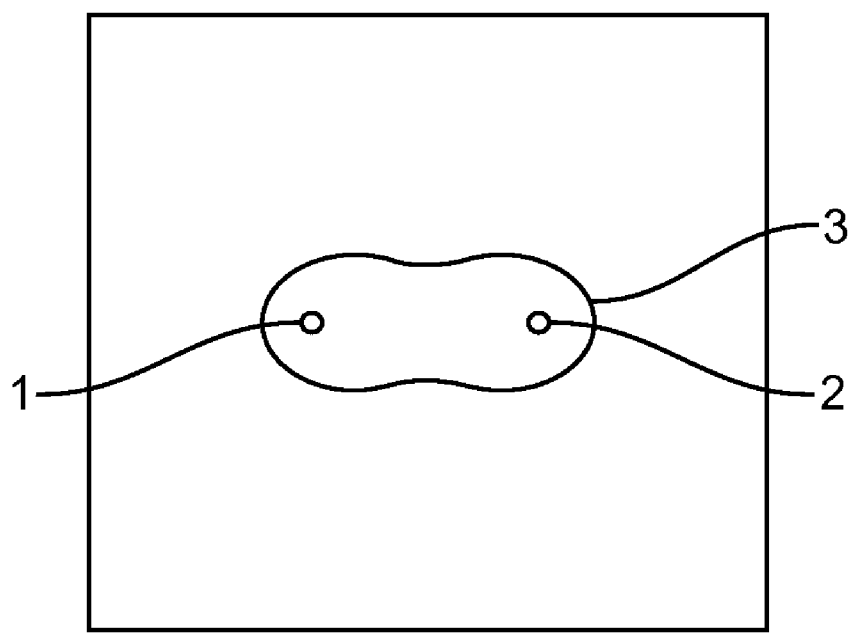

The effect of blood flow and metabolism on the extent of irreversible electroporation is illustrated in FIG. 8. The figures compare a situation with metabolism and a relatively high blood flow rate to a situation without blood flow or metabolism. It is obvious that metabolism and blood perfusion have a negligible effect on the possible extent of irreversible tissue electroporation. This is because the effect of the Joule heating produced by the electroporation current is substantially larger than the effects of blood flow or metabolism.

An even more conservative estimate for the thermal damage can be obtained by assuming that the tissue reaches 50° C. instantaneously, during the electroporation pulses such that the damage is defined as $$\Omega = t_p \xi e^{-AE/RT} \quad (10)$$

Several values taken from the literature for activation energy and frequency factor were applied to equation (10) with the pulse lengths calculated in the examples above. Because the application of the pulse is so short, the damage would be near zero, many times less than the value ($\Omega$=0.53) to induce a first degree burn (Diller, K. R., *Modeling of bioheat transfer processes at high and low temperatures*, in *Bioengineering heat transfer*, Y. I. Choi, Editor. 1992, Academic Press, Inc: Boston. p. 157-357) regardless of the values used for activation energy and frequency factor.

Currently, tissue ablation by electroporation is produced through the use of cytotoxic drugs injected in tissue combined with reversible electroporation, a procedure known as electrochemotherapy. The present invention shows that irreversible electroporation by itself produces substantial tissue ablation for the destruction of undesirable tissues in the body. The concern was that higher voltages required for irreversible electroporation would cause Joule heating and would induce thermal tissue damage to a degree that would make irreversible electroporation a marginal effect in tissue ablation. Using a mathematical model for calculating the electrical potential and temperature field in tissue during electroporation, the present invention shows that the area ablated by irreversible tissue electroporation prior to the onset of thermal effects is substantial and comparable to that of other tissue ablation techniques such as cryosurgery. Our earlier studies have shown that the extent of electroporation can be imaged in real time with electrical impedance tomography (Davalos, R. V., B. Rubinsky, and D. M. Otten, *A feasibility study for electrical impedance tomography as a means to monitor tissue electroporation for molecular medicine*. IEEE Transactions on Biomedical Engineering, 2002. 49(4): p. 400-403; Davalos, R. V., et al., *Electrical impedance tomography for imaging tissue electroporation*. IEEE Transactions on Biomedical Engineering, 2004). Irreversible electroporation, therefore, has the advantage of being a tissue ablation technique, which is as easy to apply as high temperature ablation, without the need for adjuvant chemicals as required in electrochemical ablation and electrochemotherapy. In addition, a unique aspect of irreversible electroporation is that the affected area can be controlled in real time with electrical impedance tomography.

Example 2

This example was developed to produce a correlation between electroporation pulses and thermal effects. The system analyzed is an infinitesimally small control volume of tissue exposed to an electroporation voltage gradient of V (Volts/cm). The entire electrical energy is dissipated as heat and there is no conduction of heat from the system. The calculations produce the increase in temperature with time during the application of the pulse and the results are a safe lower limit for how long a certain electroporation pulse can be administered until a certain temperature is reached. To generate the correlation an energy balance is made on a control volume between the Joule heating produced from the dissipation of heat of the V (volt/cm) electrical potential gradient (local electrical field) dissipating through tissue with an electrical conductivity of $\sigma$ (ohm-cm) and the raise in temperature of the control volume made of tissue with a density $\rho$ (g/cc) and specific heat, c, (J/g K). The calculation produces the following equation for the raise in temperature (T) per unit time (t) as a function of the voltage gradients and the thermal and electrical properties of the liver.

$$\frac{dT}{dt} = \frac{V^2 \sigma}{\rho c} \quad (2\text{-}1)$$

The table below was obtained for the liver with the following properties:
Electrical resistivity of liver—8.33 Ohm-meter
Specific heat of liver—J/g K
Density of liver—1 g/cc
We obtain the following table:

TABLE 1

| Voltage Gradient - V (V/cm) | Time per degree C. rise (ms) | time from 37 C. to 65 C. (ms) |
|---|---|---|
| 50 | 1199.52 | 33586.56 |
| 100 | 299.88 | 8396.64 |
| 150 | 133.28 | 3731.84 |
| 200 | 74.97 | 2099.16 |
| 250 | 47.98 | 1343.46 |
| 300 | 33.32 | 932.96 |
| 350 | 24.48 | 685.44 |
| 400 | 18.74 | 524.79 |
| 450 | 14.81 | 414.65 |
| 500 | 12.00 | 335.87 |
| 550 | 9.91 | 277.57 |
| 600 | 8.33 | 233.24 |
| 650 | 7.10 | 198.74 |
| 700 | 6.12 | 171.36 |
| 750 | 5.33 | 149.27 |
| 800 | 4.69 | 131.20 |
| 850 | 4.15 | 116.22 |
| 900 | 3.70 | 103.66 |
| 950 | 3.32 | 93.04 |
| 1000 | 3.00 | 83.97 |
| 1050 | 2.72 | 76.16 |
| 1100 | 2.48 | 69.39 |
| 1150 | 2.27 | 63.49 |
| 1200 | 2.08 | 58.31 |
| 1250 | 1.92 | 53.74 |
| 1300 | 1.77 | 49.68 |
| 1350 | 1.65 | 46.07 |
| 1400 | 1.53 | 42.84 |
| 1450 | 1.43 | 39.94 |
| 1500 | 1.33 | 37.32 |

The second column of Table 1 gives the amount of time it takes for the temperature of the liver to raise 1 C, when the tissue experiences the electroporation pulse in column 1. The time for even a relatively high electroporation voltage of 1500 V/cm is of the order of 1.33 millisecond for 1 C rise and 37.32 millisecond until a temperature of 65 C is reached. Using the equation (2-1) or Table 1 it is possible to evaluate the amount of time a certain pulse can be applied without inducing thermal effects. Considering the typical electroporation parameters reported so far there is no limitation in the electroporation length from thermal considerations. Column 3 of Table 1 shows the time required to reach 65 C, which is where thermal damage may begin. The calculations in this example give a lower limit for the extent of time in which a certain thermal effects will be induced by electroporation pulses. For more precise calculations it is possible to use the equation developed in this example with equation (9) or (10) from Example 1.

Example 3

Figure 9:
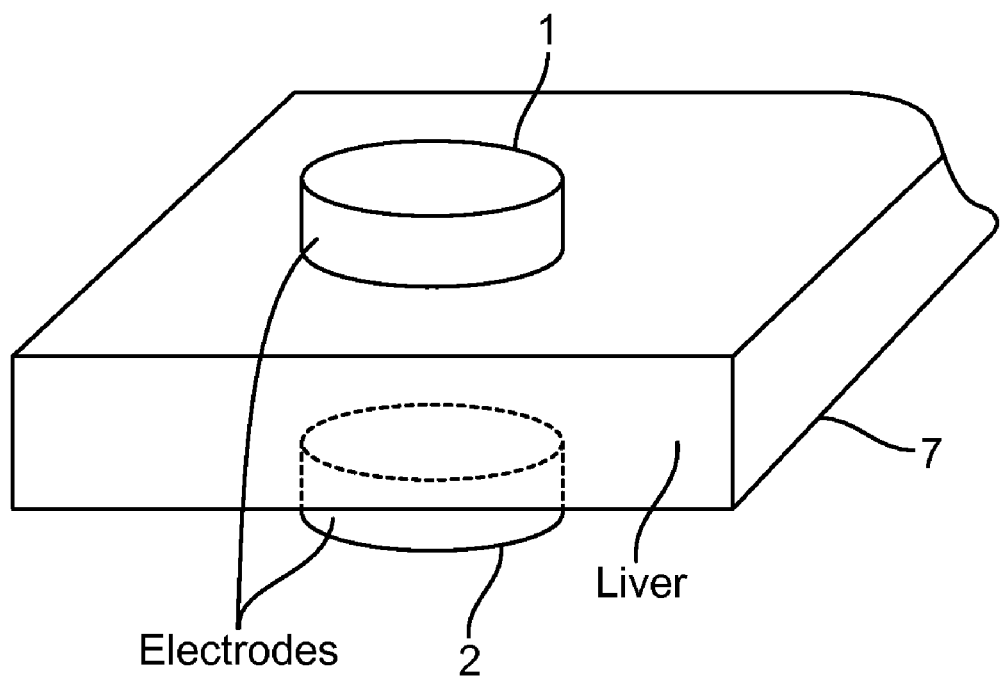
FIG. 9 is a schematic view of a liver between two cylindrical Ag/AgCl electrodes. The distance between the electrodes was 4 mm and the radius of the electrodes is 10 mm The electrodes were clamped with special rig parallel and concentric to each other. The liver lobe was compressed between the electrodes to achieve good contact.
Figure 10:
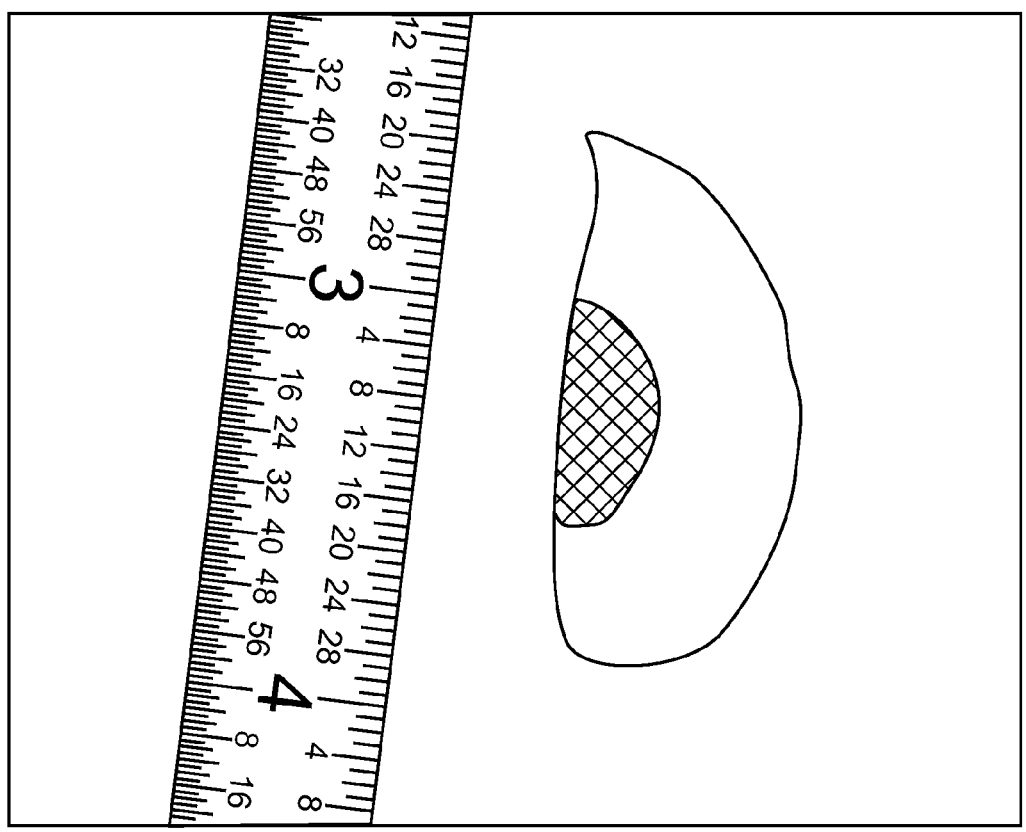
FIG. 10 is a photo of a view of a liver which was electroporated by irreversible electroporation with two cylindrical surface electrodes of 10 mm in diameter. Histology shows that the dark area is necrotic.
Figure 11:
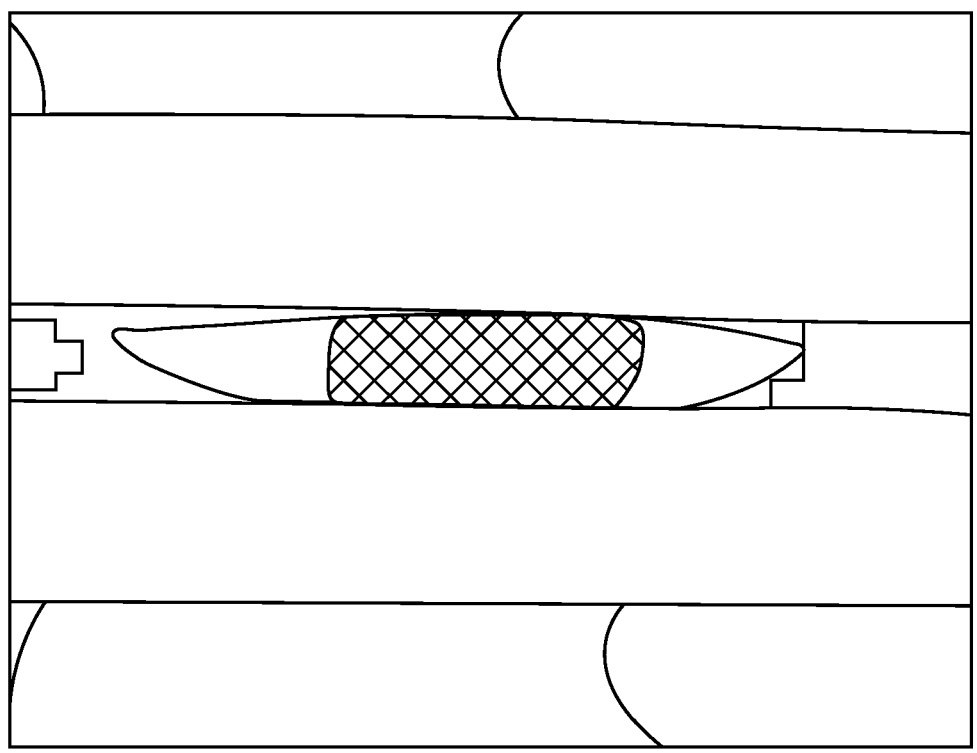
FIG. 11 is a photo of a cross section through an electroporated liver. Histology shows that the dark area is necrotic. The distance between the two Al plates that hold the liver is exactly 4 mm. The electroporation electrodes were 10 mm in diameter and centered in the middle of the lesion.
Figure 12:
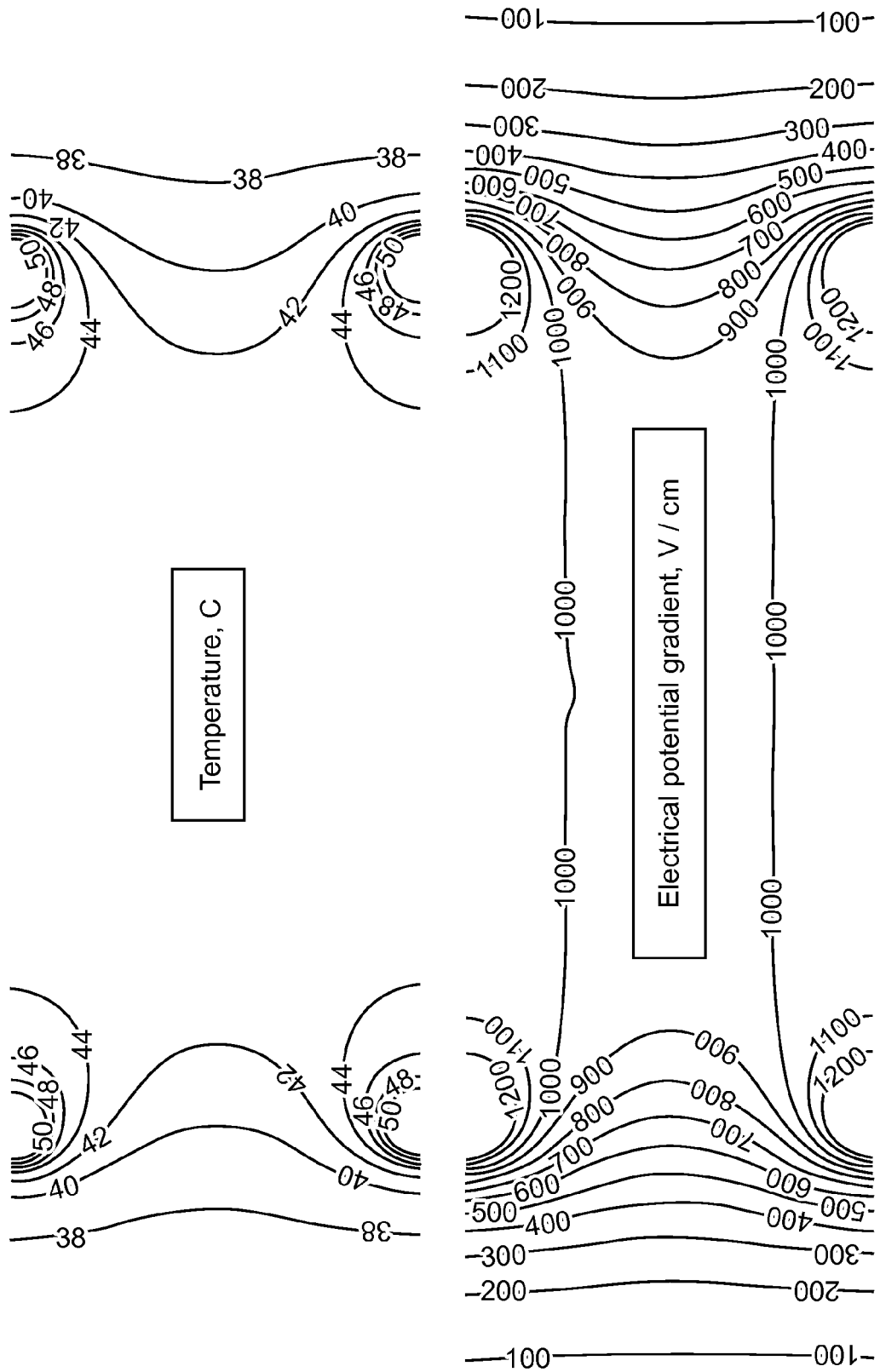
FIG. 12 shows the liver of calculated temperature distribution (C), upper panel, and electrical potential gradient (electroporation gradient) (V/cm), lower panel, for the in vivo experiment. The FIG. 12 also shows conditions through a cross section of a liver slab through the center of the electroporated area. Height of the slab is 4 mm.
Figure 13:
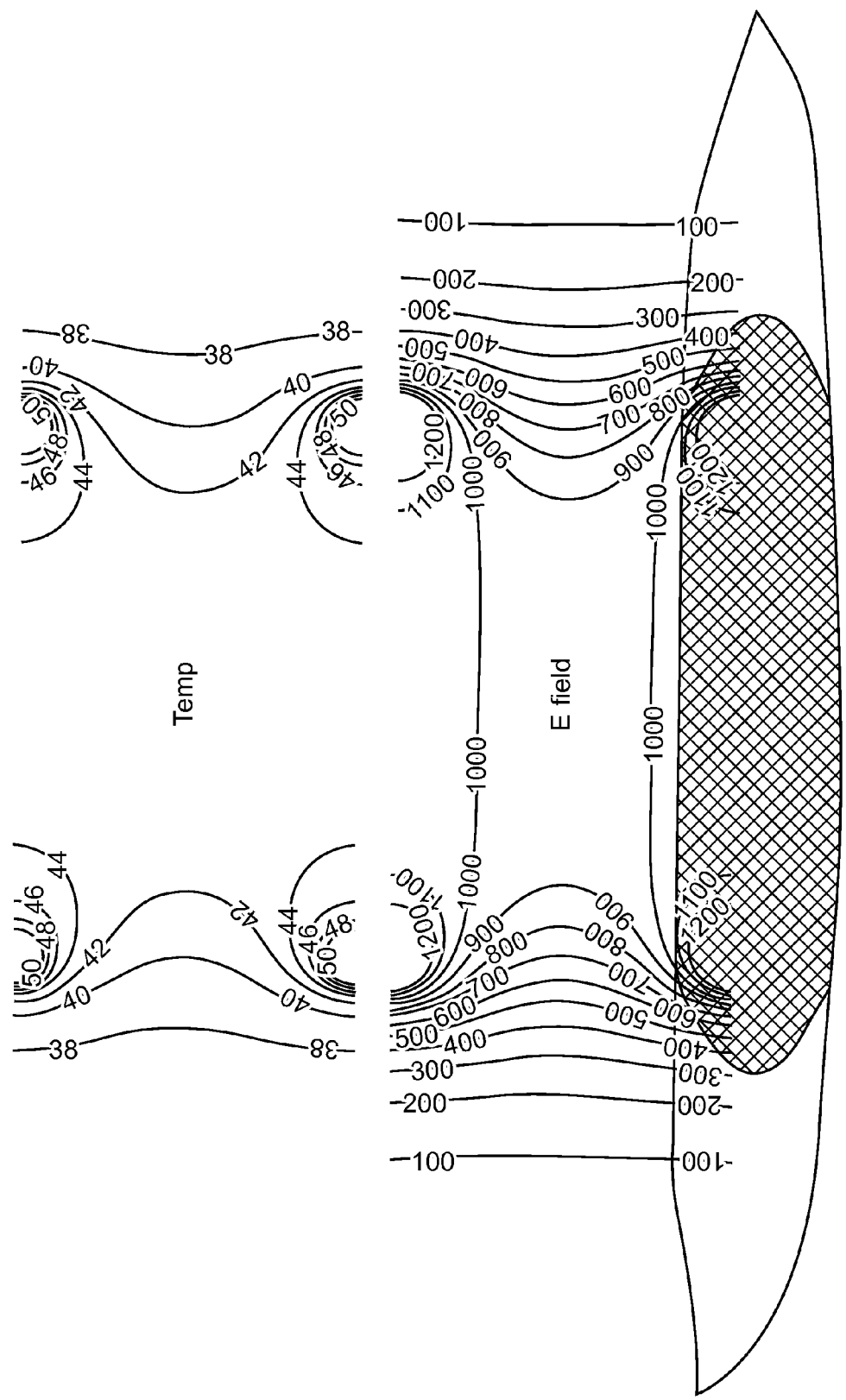
FIG. 13 combines FIGS. 11 and 12 to show a comparison between the extent of tissue necrosis (dark area) and the temperature and voltage gradient distribution in the electroporated tissue. The photo of FIG. 11 is shown schematically at the bottom on FIG. 13. It is evident that most of the dark area was at a temperature of about 42 C following the 40 milliseconds electroporation pulse. The edge of the dark area seems to correspond to the 300 V/cm electroporation gradient line.

The goal of this experiment was to verify the ability of irreversible electroporation pulses to produce substantial tissue ablation in the non-thermal regime. To this end we have performed experiments on the liver of Spraque-Dawley male rats (250 g to 350 g) under an approved animal use and care protocol. After the animals were anesthetized by injection of Nembutal Sodium Solution (50 mg/ml Pentobarbital) the liver was exposed via a midline incisions and one lobed clamped between two cylindrical electrodes of Ag/AgCl, with a diameter of 10 mm (In Vivo Metric, Healdsburg, Calif.). The electrodes had their flat surface parallel; they were concentric and the liver between the electrodes was compressed so that the lobes were separated by 4 mm. A schematic of the electrodes and the liver is shown in FIG. 9. The liver was exposed to a single electroporation pulse of 40 milliseconds. One electrode was set to 400 V and the other grounded. The rest of the liver was not in contact with any media and therefore is considered electrically insulated. After electroporation the rat was maintained under controlled anesthesia for three hours. Following exsanguination the liver was flushed with physiological saline under pressure and fixed by perfusion with formaldehyde. The liver was resected through the center of the electroporated region and analyzed by histology. FIGS. 10 and 11 show the appearance of the liver. Histology has determined that the dark area corresponds to the region of tissue necrosis. The electrical field in the electroporated liver and the temperature distribution were calculated using the equations in Example 1, subject to one electrode at a voltage of 400V and the other grounded, for 40 milliseconds. The liver was modeled as an infinite slab of 4 mm thickness, with concentric cylindrical electrodes (see FIG. 9). The results are shown in FIG. 12. FIG. 12 shows lines of constant voltage gradients (V/cm) and lines of constant temperature. It is evident that in the majority of the electroporated tissue the temperature is about 42 C immediately after the pulse. The highest temperature occurs near the edge of the cylindrical electrodes, where it is about 50 C. FIG. 13 was obtained by bringing together FIGS. 11 and 12. Superimposing the calculated results on the histological measurements reveals that the dark (necrotic) area margin corresponds to electroporation parameters of about 300 V/cm. The results demonstrate that irreversible electroporation can induce substantial tissue necrosis without the need for chemical additives as in electrochemotherapy and without a thermal effect.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of ablating tissue cells by non-thermal irreversible electroporation, comprising the steps of:
   identifying tissue to be ablated;
   placing one or more electrodes near the identified tissue;
   applying electrical pulses through the one or more electrodes in an amount which is sufficient to induce irreversible electroporation of cells of the identified tissue, but which is insufficient to induce thermal damage to substantially all of the identified tissue such that the identified tissue cells are killed by irreversible electroporation.

2. The method of claim 1, wherein the step of applying includes applying the electrical pulses in an amount which has been predetermined to maintain the temperature of the target tissue at 50° C. or less.

3. The method of claim 1, wherein the step of applying includes applying the electrical pulses in an amount which has been predetermined to maintain the temperature of the target tissue at 65° C. or less.

4. The method of claim 1, wherein the step of applying includes applying the electrical pulses in an amount which has been predetermined to maintain the temperature of the target tissue at 100° C. or less.

5. The method of claim 1, wherein the step of applying includes applying the electrical pulses in an amount which has been predetermined to maintain the temperature of at least one of the one or more electrodes below a predetermined temperature.

6. The method of claim 1, wherein the step of applying includes applying the electrical pulses in an amount which has been predetermined to be insufficient to induce thermal damage based on a bioheat equation.

7. The method of claim 6, wherein the step of applying includes applying the electrical pulses in an amount which has been predetermined to be insufficient to induce thermal damage based on a modified Penne's bioheat equation.

8. The method of claim 6, wherein the step of applying includes applying the electrical pulses in an amount which has been predetermined to be insufficient to induce thermal damage based on an Arrhenius bioheat equation.

9. The method of claim 6, wherein the step of applying includes applying the electrical pulses in an amount which has been predetermined to be insufficient to induce thermal damage based on both a modified Penne's bioheat equation and an Arrhenius bioheat equation.

10. The method of claim 1, wherein the step of applying includes applying the electrical pulses in an amount which has been predetermined to be sufficient to induce irreversible electroporation based on a transmembrane potential required for irreversible electroporation of the tissue to be ablated.

11. The method of claim 1, wherein the step of applying includes applying the electrical pulses at a rate of about 1 Hz.

12. The method of claim 1, wherein the step of applying includes applying each electrical pulse having a pulse length of greater than 5 microseconds and less than or equal to 62,000 milliseconds.

13. The method of claim 1, wherein the step of applying includes applying each electrical pulse having a pulse length of between 75 microseconds and 20,000 milliseconds.

14. The method of claim 1, wherein the step of applying includes applying each electrical pulse having a pulse length of 100 microseconds±10 microseconds.

15. The method of claim 1, wherein the step of applying includes applying each electrical pulse having a pulse length of between 75 microseconds and 20 seconds.

16. The method of claim 1, further comprising detecting that irreversible electroporation of the tissue to be ablated has occurred.

17. The method of claim 16, wherein the step of detecting includes monitoring the electrical impedance of the tissue to be ablated to detect the occurrence of irreversible electroporation.

18. The method of claim 1, further comprising detecting that irreversible electroporation of the tissue to be ablated has occurred based on electrical impedance tomography.

19. The method of claim 1, further comprising:
continuously detecting an electrical resistance of the identified tissue; and
adjusting at least one pulse parameter to achieve irreversible electroporation of the identified tissue based on the detected electrical resistance.

20. The method of claim 1, further comprising:
continuously detecting a current flowing through the one or more electrodes; and
adjusting at least one pulse parameter to achieve irreversible electroporation of the identified tissue based on the detected current flow.

21. A method of ablating tissue cells by non-thermal irreversible electroporation, comprising the steps of:
identifying tissue to be ablated in a living mammal;
placing a plurality of electrodes near the identified tissue; and
applying, through the placed electrodes, electrical pulses to the identified tissue in the living mammal, in an amount which has been predetermined to be sufficient to induce irreversible electroporation of substantially all cells of the identified tissue, but which has been predetermined to be insufficient to induce thermal damage to substantially all cells of the identified tissue such that substantially all of the identified tissue cells are ablated by non-thermal irreversible electroporation, wherein each of the electrical pulses has a pulse duration of at least 5 microseconds.

22. The method of claim 21, wherein the step of applying includes applying the electrical pulses in an amount which has been predetermined to maintain the temperature of the target tissue at 50° C. or less.

23. The method of claim 21, wherein the step of applying includes applying the electrical pulses in an amount which has been predetermined to maintain the temperature of the target tissue at 65° C. or less.

24. The method of claim 21, wherein the step of applying includes applying the electrical pulses in an amount which has been predetermined to maintain the temperature of the target tissue at 100° C. or less.

25. The method of claim 21, wherein the step of applying includes applying the electrical pulses in an amount which has been predetermined to maintain the temperature of at least one of the one or more electrodes below a predetermined temperature.

26. The method of claim 21, wherein the step of applying includes applying the electrical pulses in an amount which has been predetermined to be insufficient to induce thermal damage based on a bioheat equation.

27. The method of claim 26, wherein the step of applying includes applying the electrical pulses in an amount which has been predetermined to be insufficient to induce thermal damage based on a modified Penne's bioheat equation.

28. The method of claim 26, wherein the step of applying includes applying the electrical pulses in an amount which has been predetermined to be insufficient to induce thermal damage based on an Arrhenius bioheat equation.

29. The method of claim 26, wherein the step of applying includes applying the electrical pulses in an amount which has been predetermined to be insufficient to induce thermal damage based on both a modified Penne's bioheat equation and an Arrhenius bioheat equation.

30. The method of claim 21, wherein the step of applying includes applying the electrical pulses in an amount which has been predetermined to be sufficient to induce irreversible electroporation based on a transmembrane potential required for irreversible electroporation of the tissue to be ablated.

31. The method of claim 21, wherein the step of applying includes applying the electrical pulses at a rate of about 1 Hz.

32. The method of claim 21, wherein the step of applying includes applying each electrical pulse having a pulse length of greater than 5 microseconds and less than or equal to 62,000 milliseconds.

33. The method of claim 21, wherein the step of applying includes applying each electrical pulse having a pulse length of between 75 microseconds and 20,000 milliseconds.

34. The method of claim 21, wherein the step of applying includes applying each electrical pulse having a pulse length of 100 microseconds±10 microseconds.

35. The method of claim 21, wherein the step of applying includes applying each electrical pulse having a pulse length of between 75 microseconds and 20 seconds.

36. The method of claim 21, further comprising detecting that irreversible electroporation of the tissue to be ablated has occurred.

37. The method of claim 36, wherein the step of detecting includes monitoring the electrical impedance of the tissue to be ablated to detect the occurrence of irreversible electroporation.

38. The method of claim 21, further comprising detecting that irreversible electroporation of the tissue to be ablated has occurred based on electrical impedance tomography.

39. The method of claim 21, further comprising:
continuously detecting an electrical resistance of the identified tissue; and
adjusting at least one predetermined pulse parameter to achieve irreversible electroporation of the identified tissue based on the detected electrical resistance.

40. The method of claim 21, further comprising:
continuously detecting a current flowing through the one or more electrodes; and
adjusting at least one predetermined pulse parameter to achieve irreversible electroporation of the identified tissue based on the detected current flow.

* * * * *